(12) United States Patent  (10) Patent No.: US 6,538,016 B2
Zeller et al.  (45) Date of Patent: Mar. 25, 2003

(54) α-SULFIN-AND α-SULFONAMINO ACID AMIDES

(75) Inventors: Martin Zeller, Baden; André Jeanguenat, Basel, both of (CH); Clemens Lamberth, Efringen-Kirchen (DE)

(73) Assignee: Syngenta Participations AG, Basel (CH)

( * ) Notice: Subject to any disclaimer, the term of this patent is extended or adjusted under 35 U.S.C. 154(b) by 129 days.

(21) Appl. No.: 09/872,577

(22) Filed: Jun. 1, 2001

(65) Prior Publication Data

US 2002/0082452 A1 Jun. 27, 2002

Related U.S. Application Data

(63) Continuation of application No. PCT/EP99/09350, filed on Dec. 1, 1999.

(30) Foreign Application Priority Data

Dec. 3, 1998 (GB) ............................................. 9826650

(51) Int. Cl.[7] ...................... A61K 31/16; A61K 31/18; A61K 31/40

(52) U.S. Cl. ...................... 514/424; 514/274; 514/347; 514/367; 514/375; 514/427; 514/438; 514/471; 514/600; 514/604; 514/605; 514/607; 544/408; 546/294; 546/295; 548/217; 548/180; 548/542; 548/561; 549/77; 549/496; 564/84; 564/85; 564/86; 564/87; 564/88; 564/89; 564/90; 564/91; 564/97; 564/99

(58) Field of Search .................. 514/274, 347, 514/367, 375, 424, 427, 438, 471, 600, 604, 605, 607; 544/408; 546/294, 295; 548/217, 180, 542, 561; 549/77, 496; 564/84, 85, 86, 87, 88, 89, 90, 91, 97, 99

(56) References Cited

U.S. PATENT DOCUMENTS 6,221,888 B1 * 4/2001 Durette et al. ............... 514/357

FOREIGN PATENT DOCUMENTS

WO  WO 98 38161  9/1998
WO  WO 99 07674  2/1999

* cited by examiner

Primary Examiner—Peter O'Sullivan
(74) Attorney, Agent, or Firm—William A. Teoli, Jr.; Rose M. Allen

(57) ABSTRACT

The invention relates to α-sulfin- and α-sulfonamino acid amides of the general formula I (I)

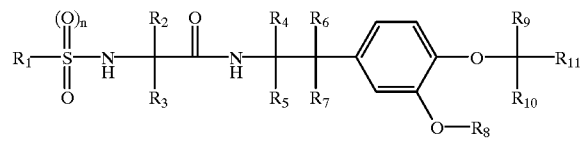

including the optical isomers thereof and mixtures of such isomers,
wherein
n is a number zero or one;
$R_1$ is $C_1$–$C_{12}$alkyl, $C_1$–$C_{12}$alkyl substituted with $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl; or a group $NR_{12}R_{13}$ wherein $R_{12}$ and $R_{13}$ are each independently of the other hydrogen or $C_1$–$C_6$-alkyl, or together are tetra- or penta-methylene;
$R_2$ and $R_3$ are each independently hydrogen; $C_1$–$C_8$alkyl; $C_1$–$C_8$alkyl substituted with hydroxy, mercapto, $C_1$–$C_4$alkoxy or $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl; or the two groups $R_2$ and $R_3$ together with the carbon atom to which they are bonded form a three- to eight-membered hydrocarbon ring;
$R_4$, $R_5$, $R_6$ and $R_7$ are each independently hydrogen or $C_1$–$C_4$alkyl;
$R_8$ is $C_1$–$C_6$alkyl, $C_3$–$C_6$alkenyl or $C_3$–$C_6$alkynyl;
$R_9$ and $R_{10}$ are each independently hydrogen or $C_1$–$C_4$alkyl; and
$R_{11}$ is either

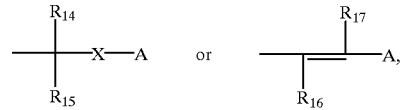

in wherein
$R_{14}$, $R_{,15}$, $R_{16}$ and $R_{17}$ are each independently hydrogen or $C_1$–$C_4$alkyl,
X is oxygen, sulfur or —$NR_{18}$—, wherein $R_{18}$ is hydrogen or $C_1$–$C_4$alkyl, and
A is optionally substituted mono- or polycylic aryl or heteroaryl, and
to the preparation of those substances and to agrochemical compositions comprising at least one of those compounds as active ingredient. The invention relates also to the preparation of compositions and to the use of the compounds or of the compositions in controlling or preventing the infestation of plants by phytopathogenic microorganisms, especially fungi.

13 Claims, No Drawings

α-SULFIN- AND α-SULFONAMINO ACID AMIDES

This application is a continuation of PCT/EP99/09350, filed Dec. 1, 1999.

The present invention relates to novel α-sulfin- and α-sulfonamino acid amides of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to α-sulfin- and α-sulfonamino acid amides of the general formula I

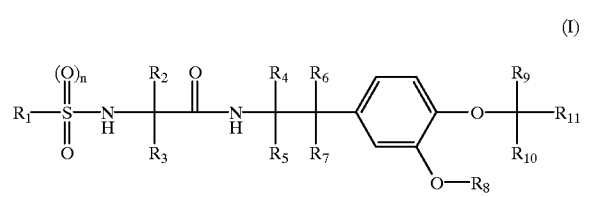

(I)

including the optical isomers thereof and mixtures of such isomers,
wherein
  n is a number zero or one;
  $R_1$ is $C_1$–$C_{12}$alkyl, $C_1$–$C_{12}$alkyl substituted with $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl; or a group $NR_{12}R_{13}$ wherein $R_{12}$ and $R_{13}$ are each independently of the other hydrogen or $C_1$–$C_6$-alkyl, or together are tetra- or penta-methylene;
  $R_2$ and $R_3$ are each independently hydrogen; $C_1$–$C_8$alkyl; $C_1$–$C_8$alkyl substituted with hydroxy, mercapto, $C_1$–$C_4$alkoxy or $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl; or the two groups $R_2$ and $R_3$ together with the carbon atom to which they are bonded form a three- to eight-membered hydrocarbon ring;
  $R_4$, $R_5$, $R_6$ and $R_7$ are each independently hydrogen or $C_1$–$C_4$alkyl;
  $R_8$ is $C_1$–$C_6$alkyl, $C_3$–$C_6$alkenyl or $C_3$–$C_6$alkynyl;
  $R_9$ and $R_{10}$ are each independently hydrogen or $C_1$–$C_4$alkyl; and
  $R_{11}$ is either

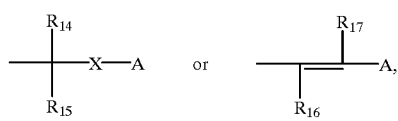

in wherein
  $R_{14}$, $R_{15}$, $R_{16}$ and $R_{17}$ are each independently hydrogen or $C_1$–$C_4$alkyl,
  X is oxygen, sulfur or —$NR_{18}$—, wherein $R_{18}$ is hydrogen or $C_1$–$C_4$alkyl, and
  A is optionally substituted mono- or polycylic aryl or heteroaryl.

In the above definition aryl includes aromatic hydrocarbon rings like phenyl, naphthyl, anthracenyl, phenanthrenyl, with phenyl being preferred.

Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; alkynyloxycarbonyl.

In the above definitions "halogen" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl.

A haloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2C_5$, $CH_2Br$, $CHClBr$, $CF_3CH_2$, etc.

Where $R_2$ and $R_3$ together with the carbon atom to which they are attached form a hydrocarbon ring the ring corresponds to cyclopropane, cyclobutane, cyclopentane, cyclohexane, cycloheptane or cyclooctane The presence of at least one asymmetric carbon atom and/or at least one asymmetric oxidized sulfur atom in the compounds of formula I means that the compounds may occur in optically isomeric forms. As a result of the presence of a possible aliphatic C=C double bond, geometric isomerism may also occur. Formula I is intended to include all those possible isomeric forms and mixtures thereof.

Preferred subgroups of compounds of formula I are those wherein n is one; or $R_1$ is $C_1$–$C_{12}$alkyl, $C_1$–$C_{12}$alkyl substituted with $C_1$–$C_4$alkoxy, $C_1$–$C_4$alkylthio, or $C_1$–$C_4$alkylsulfonyl; $C_2$–$C_{12}$alkenyl; $C_2$–$C_{12}$alkynyl; $C_1$–$C_{12}$haloalkyl; or a group $NR_{12}R_{13}$ wherein $R_{12}$ and $R_{13}$ are each independently of the other hydrogen or $C_1$–$C_6$-alkyl, or together are tetra- or penta-methylene; or $R_1$ is $C_1$–$C_{12}$alkyl, $C_2$–$C_{12}$alkenyl; $C_1$–$C_{12}$haloalkyl; or a group $NR_{12}R_{13}$ wherein $R_{12}$ and $R_{13}$ are each independently of the other hydrogen or $C_1$–$C_6$-alkyl; or $R_1$ is $C_1$–$C_4$alkyl, $C_2$–$C_4$alkenyl; $C_1$–$C_4$haloalkyl; or $C_1$–$C_2$-dialkylamino; or $R_1$ is $C_1$–$C_4$alkyl, vinyl; $C_1$–$C_4$haloalkyl; or dimethylamino; or $R_2$ is hydrogen and $R_3$ is $C_1$–$C_8$alkyl; $C_1$–$C_8$alkyl substituted with hydroxy, mercapto, $C_1$–$C_4$alkoxy or $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl; or $R_2$ is hydrogen and $R_3$ is $C_1$–$C_4$alkyl; $C_3$–$C_4$alkenyl or cyclopropyl; or $R_2$ is hydrogen and $R_3$ is $C_3$–$C_4$alkyl; allyl or cyclopropyl; or $R_2$ is hydrogen and $R_3$ is isopropyl; or $R_4$ is hydrogen or $C_1$–$C_4$alkyl and $R_5$, $R_6$ and $R_7$ are each hydrogen; or $R_4$ is hydrogen, methyl or ethyl and $R_5$, $R_6$ and $R_7$ are each hydrogen; or $R_4$ is hydrogen or methyl and $R_5$, $R_6$ and $R_7$ are each hydrogen; or $R_4$, $R_5$, $R_6$ and $R_7$ are each hydrogen; or $R_8$ is $C_1$–$C_6$alkyl; or $R_8$ is methyl or ethyl; or $R_8$ is methyl; or $R_9$, $R_{10}$, $R_{14}$, $R_{15}$, $R_{16}$, $R_{17}$ are each independently hydrogen or methyl; or $R_9$, $R_{10}$, $R_{14}$, $R_{15}$, $R_{16}$, $R_{17}$ are each hydrogen; or X is oxygen, sulfur or —$NR_8$—, wherein $R_{18}$ is hydrogen or methyl; or X is oxygen, sulfur or —NH—; or X is oxygen; or A is optionally substituted heteroaryl consisting of one or two five to six membered rings containing one to four identical or different heteroatoms selected from oxygen, nitrogen and sulfur; or A is phenyl, naphthyl, furyl, thienyl, pyrrolyl, imidazolyl, pyrazolyl, thiazolyl, oxazolyl, isoxazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl, each optionally substituted by 1 to 3 substituents selected from $C_1$–$C_8$-alkyl, $C_2$–$C_8$-alkenyl, $C_2$–$C_8$-alkynyl, $C_3$–$C_8$-cycloalkyl, $C_3$–$C_8$-cycloalkyl-$C_1$–$C_4$-alkyl, phenyl, phenyl-$C_1$–$C_4$-alkyl wherein the hydrogens of all the preceding substituents may be in turn optionally substituted by one or several same or different halogens; $C_1$–$C_8$-alkoxy; $C_3$–$C_8$-alkenyloxy; $C_3$–$C_8$-alkynyloxy; $C_1$–$C_8$-alkoxy-$C_1$–$C_4$-alkyl; $C_1$–$C_8$halogenalkoxy; $C_1$–$C_8$-alkylthio; $C_1$–$C_8$-halogenalkylthio; $C_1$–$C_8$-alkylsulfonyl; formyl; $C_2$–$C_8$-alkanoyl; hydroxy; halogen; cyano; nitro; amino; $C_1$–$C_8$-alkylamino; $C_1$–$C_8$-dialkylamino; carboxy; $C_1$–$C_8$-alkoxycarbonyl; $C_1$–$C_8$-alkenyloxycarbonyl or $C_1$–$C_8$-alkynyloxycarbonyl; or A is phenyl, naphthyl, thienyl, pyridyl, pyrimidinyl, triazinyl or quinolyl, each optionally substituted by 1 to 3 substituents selected from $C_1$–$C_8$-alkyl, $C_2$–$C_8$-alkenyl wherein the hydrogens of all the preceding substituents may be in turn optionally substituted by one or several same or different halogens; $C_1$–$C_8$-alkoxy; $C_1$–$C_8$halogenalkoxy; $C_1$–$C_8$-alkylthio; $C_1$–$C_8$-halogenalkylthio; halogen; cyano; nitro or $C_1$–$C_8$-alkoxycarbonyl; or A is phenyl or pyridyl, each optionally substituted by 1 to 3 substituents selected from $C_1$–$C_8$-alkyl; $C_1$–$C_8$-haloalkyl; $C_1$–$C_8$-alkoxy; $C_1$–$C_8$halogenalkoxy; $C_1$–$C_8$-alkylthio; $C_1$–$C_8$-halogenalkylthio; halogen; cyano; nitro or $C_1$–$C_8$-alkoxycarbonyl.

Further preferred subgroups of the compounds of formula I are those wherein $R_1$ is $C_1$–$C_{12}$alkyl, $C_1$–$C_{12}$alkyl substituted with $C_1$–$C_4$alkoxy, $C_1$–$C_4$alkylthio, or $C_1$–$C_4$alkylsulfonyl; $C_2$–$C_{12}$alkenyl; $C_2$–$C_{12}$alkynyl; $C_1$–$C_{12}$haloalkyl; or a group $NR_{12}R_{13}$ wherein $R_{12}$ and $R_{13}$ are each independently of the other hydrogen or $C_1$–$C_6$-alkyl, or together are tetra- or penta-methylene; and $R_2$ is hydrogen and $R_3$ is $C_1$–$C_8$alkyl; $C_1$–$C_8$alkyl substituted with hydroxy, mercapto, $C_1$–$C_4$alkoxy or $C_1$–$C_4$alkylthio; $C_3$–$C_8$alkenyl; $C_3$–$C_8$alkynyl; $C_3$–$C_8$cycloalkyl; $C_1$–$C_4$alkyl; and $R_4$ is hydrogen or $C_1$–$C_4$alkyl and $R_5$, $R_6$ and $R_7$ are each hydrogen; or those wherein n is one; and $R_1$ is $C_1$–$C_{12}$alkyl, $C_2$–$C_{12}$alkenyl; $C_1$–$C_{12}$haloalkyl; or a group $NR_{12}R_{13}$ wherein $R_{12}$ and $R_{13}$ are each independently of the other hydrogen or $C_1$–$C_6$-alkyl; and $R_2$ is hydrogen and $R_3$ is $C_1$–$C_4$alkyl; $C_3$–$C_4$alkenyl or cyclopropyl; and $R_4$ is hydrogen, methyl or ethyl and $R_5$, $R_6$ and $R_7$ are each hydrogen; and $R_8$ is $C_1$–$C_6$alkyl; or those wherein n is one; and $R_1$ is $C_1$–$C_4$alkyl, $C_2$–$C_4$alkenyl; $C_1$–$C_4$haloalkyl; or $C_1$–$C_2$-dialkylamino; and $R_2$ is hydrogen and $R_3$ is $C_3$–$C_4$alkyl; allyl or cyclopropyl; and $R_4$ is hydrogen or methyl and $R_5$, $R_6$ and $R_7$ are each hydrogen; and $R_8$ is methyl or ethyl; or those wherein n is one; and $R_1$ is $C_1$–$C_4$alkyl, vinyl; $C_1$–$C_4$haloalkyl; or dimethylamino; and $R_2$ is hydrogen and $R_3$ is isopropyl; and $R_4$, $R_5$, $R_6$ and $R_7$ are each hydrogen; and $R_8$ is methyl.

Amongst the above preferred subgroups of compounds of formula I in turn those are preferred wherein A is optionally substituted heteroaryl consisting of one or two five to six membered rings containing one to four identical or different heteroatoms selected from oxygen, nitrogen and sulfur; or those wherein $R_9$, $R_{10}$, $R_{14}$, $R_{16}$, $R_{17}$ are each independently hydrogen or methyl; and X is oxygen, sulfur or —$NR_{18}$—, wherein $R_{18}$ is hydrogen or methyl; and A is phenyl, naphthyl, furyl, thienyl, pyrrolyl, imidazolyl, pyrazolyl, thiazolyl, oxazolyl, isoxazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl, each optionally substituted by 1 to 3 substituents selected from $C_1$–$C_8$-alkyl, $C_2$–$C_8$-alkenyl, $C_2$–$C_8$-alkynyl, $C_3$—$C_8$-cycloalkyl, $C_3$–$C_8$-cycloalkyl-$C_1$–$C_4$-alkyl, phenyl, phenyl-$C_1$–$C_4$-alkyl wherein the hydrogens of all the preceding substituents may be in turn optionally substituted by one or several same or different halogens; $C_1$–$C_8$-alkoxy; $C_3$–$C_8$-alkenyloxy; $C_3$–$C_8$-alkynyloxy; $C_1$–$C_8$-alkoxy-$C_1$–$C_4$-alkyl; $C_1$–$C_8$halogenalkoxy; $C_1$–$C_8$-alkylthio; $C_1$–$C_8$-halogenalkylthio; $C_1$–$C_8$-alkylsulfonyl; formyl; $C_2$–$C_8$-alkanoyl; hydroxy; halogen; cyano; nitro; amino; $C_1$–$C_8$-alkylamino; $C_1$–$C_8$-dialkylamino; carboxy; $C_1$–$C_8$-alkoxycarbonyl; $C_1$–$C_8$-alkenyloxycarbonyl or $C_1$–$C_8$-alkynyloxycarbonyl; or those wherein $R_9$, $R_{10}$, $R_{14}$, $R_{15}$, $R_{16}$, $R_{17}$ are each hydrogen; and X is oxygen, sulfur or —NH—; or A is phenyl, naphthyl, thienyl, pyridyl, pyrimidinyl, triazinyl or quinolyl, each optionally substituted by 1 to 3 substituents selected from $C_1$–$C_8$-alkyl, $C_2$–$C_8$-alkenyl wherein the hydrogens of all the preceding substituents may be in turn optionally substituted by one or several same or different halogens; $C_1$–$C_8$-alkoxy; $C_1$–$C_8$halogenalkoxy; $C_1$–$C_8$-alkylthio; $C_1$–$C_8$-halogenalkylthio; halogen; cyano; nitro or $C_1$–$C_8$-alkoxycarbonyl; or those wherein $R_9$, $R_{10}$, $R_{14}$, $R_{15}$, $R_{16}$, $R_{17}$ are each hydrogen; and X is oxygen; and A is phenyl or pyridyl, each optionally substituted by 1 to 3 substituents selected from $C_1$–$C_8$-alkyl; $C_1$–$C_8$-haloalkyl; $C_1$–$C_8$-alkoxy; $C_1$–$C_8$halogenalkoxy; $C_1$–$C_8$-alkylthio; $C_1$–$C_8$-halogenalkylthio; halogen; cyano; nitro or $C_1$–$C_8$-alkoxycarbonyl.

Preferred individual compounds are:

(S)-2-ethanesulfonylamino-N-(2-{4-[2-(4-fluoro-phenoxy)-ethoxy]-3-methoxy-phenyl}-ethyl)-3-methyl-butyramide,
(S)-2-methanesulfonylamino-N-(2-{4-[2-(4-fluoro-phenoxy)-ethoxy]-3-methoxy-phenyl}-ethyl)-3-methyl-butyramide,
(S)-2-dimethylaminosulfonylamino-N-(2-{4-[2-(4-fluoro-phenoxy)-ethoxy]-3-methoxy-phenyl}-ethyl)-3-methyl-butyramide,
(S)-2-ethanesulfonylamino-N-(2-{4-[2-(4-fluoro-phenoxy)-ethoxy]-3-methoxy-phenyl}-ethyl)-butyramide,
(S)-2-ethanesulfonylamino-N-(2-{4-[2-(4-fluoro-phenoxy)-ethoxy]-3-methoxy-phenyl}-ethyl)-pentanoylamide,
(S)-2-ethanesulfonylamino-N-(2-{4-[2-phenoxy-ethoxy]-3-methoxy-phenyl}-ethyl)-butyramide,
(S)-2-ethanesulfonylamino-N-(2-{4-[2-(4-chloro-phenoxy)-ethoxy]-3-methoxy-phenyl}-ethyl)-3-methyl-butyramide,
(S)-2-ethanesulfonylamino-N-(2-{4-[2-(3-methyl-phenoxy)-ethoxy]-3-methoxy-phenyl}-ethyl)-3-methyl-butyramide,
(S)-2-ethanesulfonylamino-N-(2-{4-[2-(4-methyl-phenoxy)-ethoxy]-3-methoxy-phenyl}-ethyl)-3-methyl-butyramide,
(S)-2-ethanesulfonylamino-N-(2-{4-[2-(3-fluoro-phenoxy)-ethoxy]-3-methoxy-phenyl}-ethyl)-3-methyl-butyramide,
(S)-2-ethanesulfonylamino-N-(2-{4-[2-(2-chloro-phenoxy)-ethoxy]-3-methoxy-phenyl}-ethyl)-3-methyl-butyramide,
(S)-2-ethanesulfonylamino-N-(2-{4-[1-methyl-2-(4-chloro-phenoxy)-ethoxy]-3-methoxy-phenyl}-ethyl)-3-methyl-butyramide,
(S)-2-methanesulfonylamino-N-(2-{4-[2-(3,4-dichloro-phenoxy)-ethoxy]-3-methoxy-phenyl}-ethyl)-3-methyl-butyramide,
(S)-2-methanesulfonylamino-N-(2-{4-[2-(3-fluoro-phenoxy)-ethoxy]-3-methoxy-phenyl}-ethyl)-3-methyl-butyramide,
(S)-2-methanesulfonylamino-N-(2-{4-[2-(4-chloro-phenylthio)-ethoxy]-3-methoxy-phenyl}-ethyl)-3-methyl-butyramide,
(S)-2-methanesulfonylamino-N-(2-{4-[1-methyl-2-(4-chloro-phenoxy)-ethoxy]-3-methoxy-phenyl}-ethyl)-3-methyl-butyramide,
(S)-2-ethanesulfonylamino-N-(2-{4-[3-(4-chloro-phenyl)-allyloxy]-3-methoxy-phenyl}-ethyl)-2-cyclopropyl-acetamide,
(S)-2-ethanesulfonylamino-N-(2-{4-[2-(4-chloro-phenyl)-allyloxy]-3-methoxy-phenyl}-ethyl)-butyramide,
(S)-2-methanesulfonylamino-N-(2-{4-[2-(4-chloro-phenyl)-allyloxy]-3-methoxy-phenyl}-ethyl)-3-methyl-butyramide,
(S)-2-ethanesulfonylamino-N-(2-{4-[2-(2-fluoro-phenyl)-allyloxy]-3-methoxy-phenyl}-ethyl)-3-methyl-butyramide,
(S)-2-methanesulfonylamino-N-(2-{4-[2-(2-fluoro-phenyl)-allyloxy]-3-methoxy-phenyl}-ethyl)-3-methyl-butyramide,
(S)-2-methanesulfonylamino-N-(2-{4-[2-(4-bromo-phenyl)-allyloxy]-3-methoxy-phenyl}-ethyl)-3-methyl-butyramide,
(S)(E)-2-ethanesulfonylamino-N-(2-{4-[2-(4-chloro-phenyl)-allyloxy]-3-methoxy-phenyl}-ethyl)-3-methyl-butyramide,
(S)(Z)-2-ethanesulfonylamino-N-(2-{4-[2-(4-chloro-phenyl)-allyloxy]-3-methoxy-phenyl}-ethyl)-3-methyl-butyramide,
(S)-2-methanesulfonylamino-N-(2-{4-[2-(4-chloro-phenoxy)-ethoxy]-3-methoxy-phenyl}-ethyl)-3-methyl-butyramide,
(S)-2-ethanesulfonylamino-N-(2-{4-[2-(4-chloro-phenoxy)-ethoxy]-3-methoxy-phenyl}-ethyl)-butyramide,
(S)-2-ethanesulfonylamino-N-(2-{4-[2-(4-chloro-phenoxy)-ethoxy]-3-methoxy-phenyl}-ethyl)-pentanoylamide,
Z-(S)-2-methanesulfonylamino-N-(2-{4-[2-(4-chloro-phenoxy)-allyloxy]-3-methoxy-phenyl}-ethyl)-pentanoylamide, and
Z-(S)-2-ethanesulfonylamino-N-(2-{4-[3-phenoxy-allyloxy]-3-methoxy-phenyl}-ethyl)-3-methyl-butyramide.

Certain α-sulfin- and α-sulfonamino acid derivatives having a different kind of structure have already been proposed for controlling plant-destructive fungi (for example in WO 95/030651, WO 97/14677, WO 98/38160 and WO 98/38161). The action of those preparations is not, however, satisfactory in all aspects of agricultural needs. Surprisingly, with the compound structure of formula I, new kinds of microbicides having a high level of activity have been found.

The α-sulfin- and α-sulfonamino acid amides of formula I may be obtained according to one of the following processes:

a)

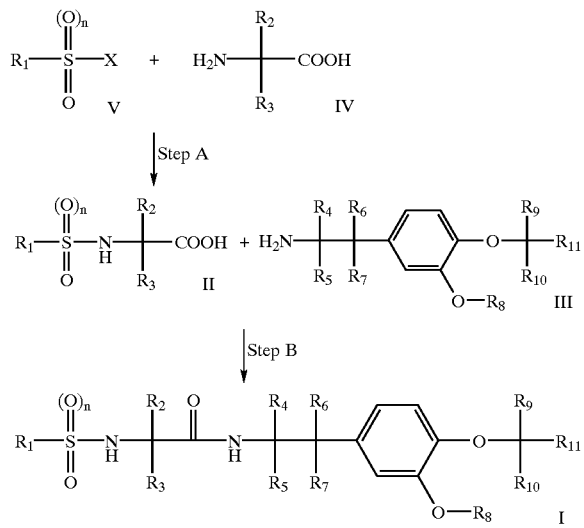

An amino acid of formula II or a carboxy-activated derivative of an amino acid of formula II wherein $R_1$, n, $R_2$ and $R_3$ are as defined for formula I is reacted with an amine of formula III wherein $R_4$, $R_5$, $R_6$, $R_7$, $R_8$, $R_9$, $R_{10}$ and $R_{11}$ are as defined above optionally in the presence of a base and optionally in the presence of a diluting agent (step B).

Carboxy-activated derivatives of the amino acid of formula II encompasses all compounds having an activated carboxyl group like an acid halide, such as an acid chloride, like symmetrical or mixed anhydrides, such as mixed anhydrides with O-alkylcarbonates, like activated esters, such as p-nitrophenylesters or N-hydroxysucinimidesters, as well as in situ produced activated forms of the amino acid of formula II by condensating agents, such as dicyclohexylcarbodiimid, carbonyidiimidazol, benzotriazol-1-yloxy-tris(dimethylamino)-phosphonium hexafluorophosphate, O-benzotriazol-1-yl N,N,N',N'-bis(pentamethylene)-uronium hexafluorophosphate, O-benzotriazol-1-yl N,N,N',N'-bis(tetramethylene)uronium hexafluorophosphate, O-benzotriazol-1-yl N,N,N',N'-tetramethyluronium hexafluoro-phosphate or benzotriazol-1-yloxy-tripyrrolidinophosphonium hexafluorophosphate. The mixed anhydrides of the amino acids of the formula II may be prepared by reaction of an amirnio acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, n-methyl-piperidine or N-methyl-morpholin.

The present reaction is preferably performed in an inert solvent like aromatic, non-aromatic or halogenated hydrocarbons, such as chlorohydrocarbons e.g. dichloromethane or toluene; ketones, e.g. acetone; esters, e.g. ethyl acetate; amides, e.g. N,N-dimethylformamide; nitrites e.g. acetonitrile; or ethers e.g. diethylether, tert-butyl-methylether, dioxane or tetrahydrofurane or water. It is also possible to use mixtures of these solvents. The reaction is preformed optionally in the presence of an organic or inorganic base like a tertiary amine, e.g. triethylamine, N,N-diisopropyl-ethylamine, pyridine, n-methyl-piperidine or N-methyl-morpholin, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

The compounds of formula II may be prepared by reaction of an amino acid of formula IV where $R_2$ and $R_3$ are as defined for formula I with a sulfonyl halide or a sulfinyl halide of formula V where $R_1$ and n have the same meanings as defined above and where X is halide, preferentially chlorine or bromine (step A).

The reaction may be performed in an inert solvent like aromatic, non-aromatic or halogenated hydrocarbons, such as chlorohydrocarbons, e.g. dichloromethane or toluene; ketones, e.g. acetone; esters, e.g. ethyl acetate; ethers, e.g. diethylether, tert-butyl-methylether, dioxane or tetrahydrofurane or water. It is also possible to use mixtures of these solvents. The reaction is performed optionally in the presence of an organic or inorganic base like a tertiary amine, such as triethylamine, N,N-diisopropyl-ethylamine, pyridine, n-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

b)

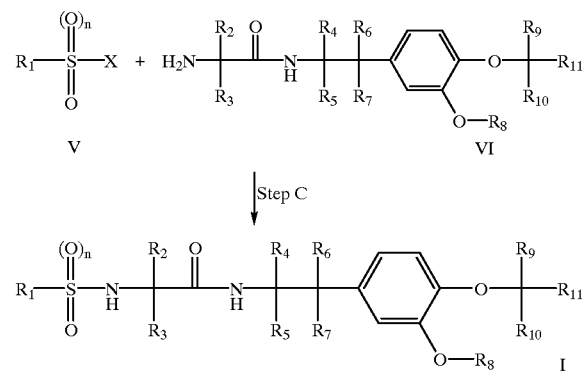

The compounds of formula I may also be prepared by reaction of an amino acid derivative of formula VI wherein $R_2$, $R_3$, $R_4$, $R_5$, $R_6$, $R_7$, $R_8$, $R_9$, $R_{10}$ and $R_{11}$ are as defined for formula I with a sulfonyl halide or a sulfinyl halide of formula V wherein $R_1$ and n are as defined for formula I and X is halide, preferentially chlorine or bromine (step C). The reaction is performed in the same manner as described for step A.

c)

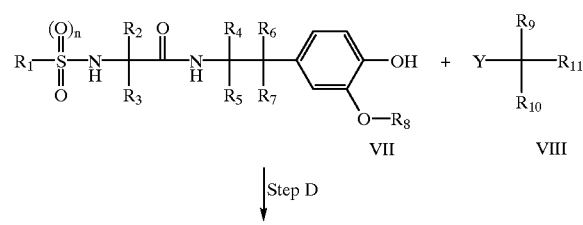

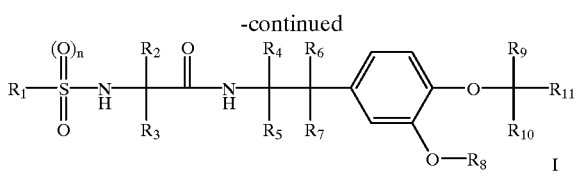

The compounds of formula I may also be prepared by reaction of a phenol of formula VII wherein $R_1$, n, $R_2$, $R_3$, $R_4$, $R_5$, $R_6$, $R_7$ and $R_8$ are as defined for formula I with a compound of formula VIII wherein $R_9$, $R_{10}$ and $R_{11}$ are as defined for formula I and Y is a leaving group like a halide such as a chloride or bromide or a sulfonic ester such as a tosylate, mesylate or triflate (step D).

The reaction may be performed in an inert solvent like aromatic, non-aromatic or halogenated hydrocarbons, such as chlorohydrocarbons e.g. dichloromethane or toluene; ketones e.g. acetone or 2-butanone; esters, e.g. ethyl acetate; ethers, e.g. diethylether, tert-butyl-methylether, dioxane or tetrahydrofurane, amides, e.g. dimethylformamide, nitrites, e.g. acetonitrile, alcohols, e.g. methanol, ethanol, isopropanol, n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

d)

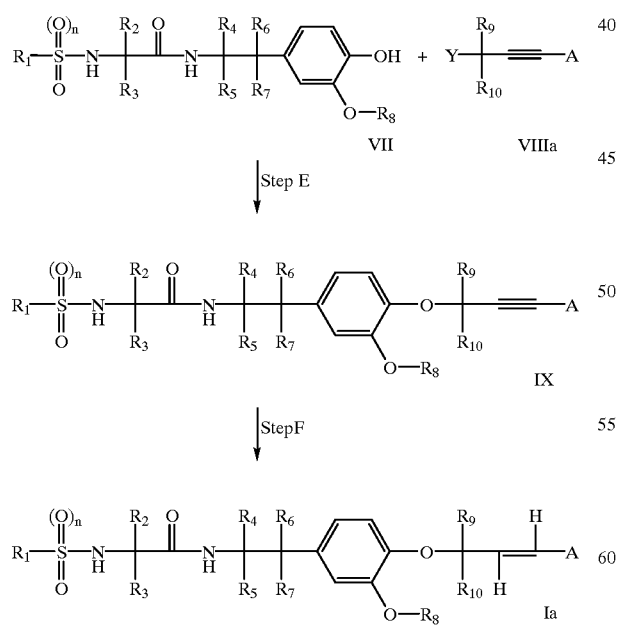

The compounds of formula Ia may also be prepared via formula IX wherein $R_1$, n, $R_2$, $R_3$, $R_4$, $R_5$, $R_6$, $R_7$, $R_8$ and A are defined for formula I by reacting of a phenol of formula VII wherein $R_1$, n, $R_2$, $R_3$, $R_4$, $R_5$, $R_6$, $R_7$ and R8 are as defined for formula I with a compound of formula VIIIa wherein $R_9$, $R_{10}$ and A are as defined for formula I and Y is a leaving group like a halide such as a chloride or bromide or a sulfonic ester such as a tosylate, mesylate or triflate (step E).

The reaction is performed in the same manner as described for step D.

The compounds of formula Ia where $R_{11}$ is (E) —CH=CH—A and A is as defined for formula I may be prepared by reaction of compounds of formula IX with hydrogen.

The reaction is performed in a solvent like ethers, e.g. diethylether, dioxane or tetrahydrofuran, or like alcohols, e.g. methanol or ethanol, or water in the presence of transition metals or transition metal salts, e.g. nickel, cobalt, palladium, platinium or rhodium, optionally in the presence of bases, e.g. ammonia, or in the presence of salts, e.g. barium sulfate, at temperatures ranging from −20° C. to +160° C. and at pressures ranging from 1 to 200 bar.

aa) The intermediate amines of formula III may be obtained by one of the following processes:

Procedure 1:

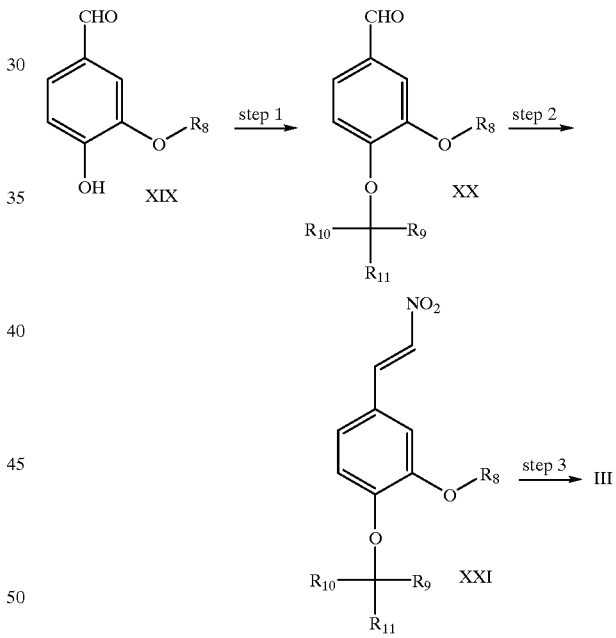

Procedure 2:

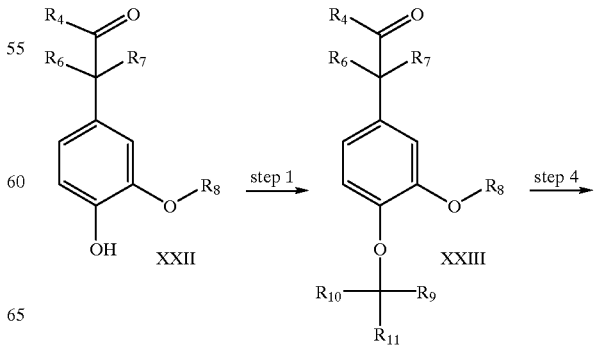

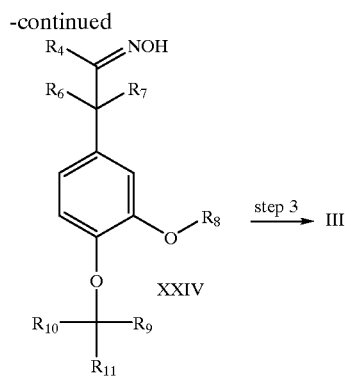

Procedure 3:

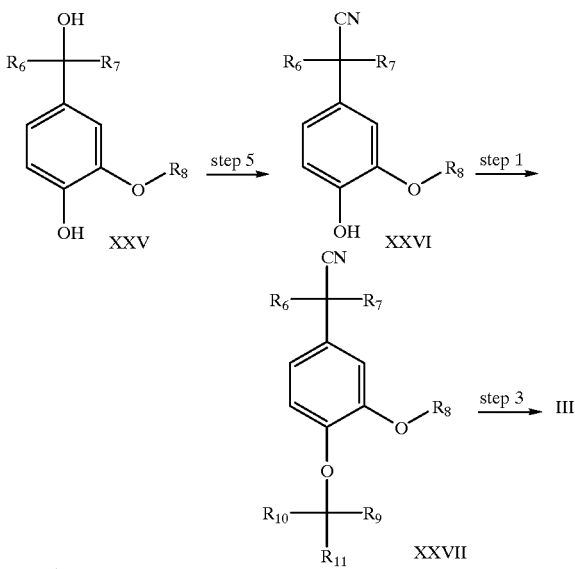

Procedure 4:

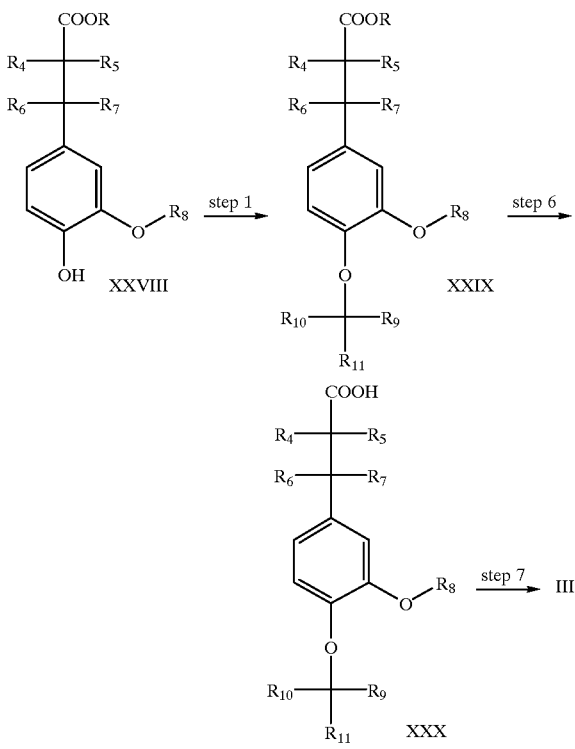

Step 1 is the alkylation of a phenol with a compound of formula VIII. The reaction is performed in the same manner as described for procedure c).

Step 2 is the reaction of an aromatic aldehyde with nitromethane. This reaction is performed in a solvent like an organic carboxylic acids, e.g. acetic acidoptionally in the presence of the ammonium salt of this carboxylic acid, e.g. ammonium acetate at temperatures ranging from 0° C. to +200° C.

Step 3 is the reduction of an unsaturated nitrogen-compound. This reaction is performed in a solvent like an ether, e.g. diethylether, dioxane or tetrahydrofuran, or an alcohol, e.g. methanol, ethanol or isopropanol, with borohydride, with a boron-complex, e.g. the complex of borohydride with tetrahyrofuran, with an alkaliborohydride, with an alkalialuminiumhydride, e.g. lithiumaluminiumhydride, with aluminiumhydride, with an aluminiumalkoxyhydride or with hydrogen optionally in the presence of a transition metal, a transition metal salt or a transition metal complex, e.g. nickel, cobalt, palladium, platinium or rhodium at temperatures ranging from −50° C. to +200° C.

Step 4 is the reaction of an aldehyde or a ketone of formula with hydroxylamine or with a salt of hydroxylamine. This reaction is performed in a solvent like an alcohol, e.g. methanol, ethanol or isopropanol, like an ether, e.g. diethylether, dioxane or tetrahydrofuran, like an amide, e.g. dimethylformamide, or in water or in a mixture of these solvents optionally in the presence of an organic or inorganic base like a tertiary amine, e.g. triethylamine, like a heterocyclic compound containing nitrogen, e.g. pyridine, or like an alkalicarbonate, e.g. sodium carbonate or potassium carbonate, at temperatures ranging from −20° C. to +150° C.

Step 5 is the exchange of hydroxy by cyanide. This reaction is performed in an organic solvent like an amide, e.g. dimethylformamide using a metal cyanide like an alkali cyanide, e.g. sodium cyanide or potassium cyanide, at temperatures ranging from 0° C. to +200° C.

Step 6 is the hydrolysis of an alkyl ester. This reaction is performed in a solvent like an alcohol, e.g. methanol, ethanol or isopropanol, like an ether, e.g. diethylether, dioxane or tetrahydrofuran, like a halogenated hydrocarbon, e.g. dichloromethane, or water or in a mixture of these solvents optionally in the presence of an alkali hydroxide, e.g. lithium hydroxide, sodium hydroxide or potassium hydroxide, or optionally in the presence of an acid, e.g. hydrogen chloride, sulfuric acid or trifluoroacetic acid at temperatures ranging from −20° C. to +160° C.

Step 7 is the reaction of a carboxylic acid or the activated form of this carboxylic acid with hydrogen azide or an azide-salt. An activated form of a carboxylic acid can be the acid halogenide, e.g. acid chloride, a symmetric or a mixed anhydride. Azide-salts can be alkali azides, e.g. sodium azide. The reaction is performed in a solvent like a hydrocarbon, e.g. toluene or xylene, like a halogenated hydrocarbon, e.g. chloroform, like an ether, e.g. dioxane, like a ketone, e.g. acetone or 2-butanone, like an alcohol, e.g. methanol, ethanol or tert-butanol, or water or in a mixture of these solvents optionally in the presence of an acid like an inorganic acid, e.g. sulfuric acid or hydrogen chloride at temperatures ranging from −40° C. to +200° C.

In a preferred form the compounds of formula XXVI are prepared starting from compounds of the formula XXV by applying step 5 and step 1 in the same pot.- bb) Amines of formula VI can be obtained by the following process:

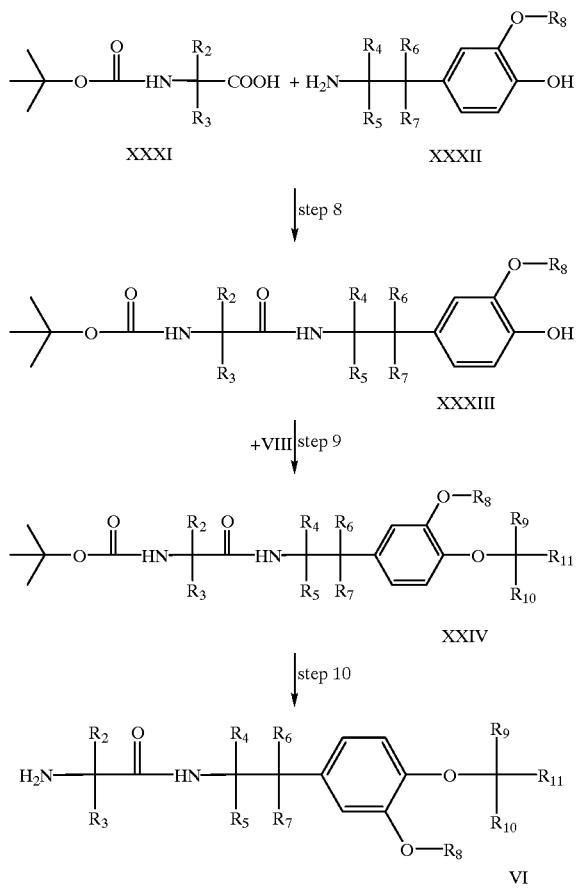

Step 8 is the amidation of an BOC protected amino acid of formula XXI with an amine of formula XXII. The reaction is performed in the same manner as described for step A.

Step 9 is the alkylation of a phenol of formula XXIIII with an compound of formula VIII. The reaction is performed in the same manner as described for step D.

Step 10 is the hydrolysis of a carbamate of formula XIX. The reaction is performed in a solvent like hydrocarbons, e.g. toluene, like halogenated hydrocarbons, e.g. dichloromethane, like ketones, e.g. acetone, like esters, e.g. ethyl acetate, like ethers, e.g. dioxane or tetrahydrofuran, or like water or in mixtures of these solvents optionally in the presence of an organic acid like carboxylic acid, e.g. trifluoroacetic acid, or like a sulfonic acid, e.g. methanesulfonic acid or toluenesulfonic acid, or in the presence of an inorganic acid, e.g. hydrogen chloride or sulfuric acid, at temperatures ranging from $-40°$ C. to $+160°$ C.

The compounds of formula I are oils or solids at room temperature and are distinguished by valuable microbicidal properties. They can be used in the agricultural sector or related fields preventively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrirridine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime; dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine or validamycin.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

Preparation Examples for Compounds of Formula I

EXAMPLE A1.1

(S)-2-Ethanesulfonylamino-N-(2-{4-[2-(4-fluoro-phenoxy)-ethoxy]-3-methoxy-phenyl}-ethyl)-3-methyl-butyramide

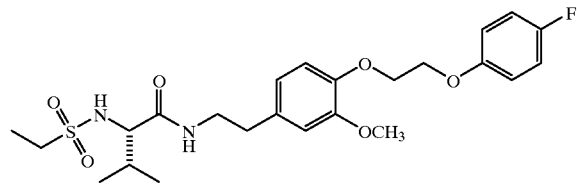

To a mixture of (S)-2-ethanesulfonylamino-3-methyl-butyric acid (0.63 g), 2-{4-[2-(4-fluoro-phenoxy)-ethoxy]-3-methoxy-phenyl}-ethylamine hydrochloride (1.0 g) and diethyl-isopropylamine (1.8 ml) in dimethylformamide (30 ml) is added benzotriazol-1-yloxy-tris-(dimethylamino) phosphonium hexafluorophosphate (1.5 g) in one portion. The reaction mixture is stirred for 2 hours at room temperature. Water (200 ml) is then added. The mixture is extracted with ethyl acetate (2×200 ml). The organic layers are washed with brine (2×200 ml), dried (MgSO$_4$) and evaporated. The residue is purified by flash column chromatography on silica gel (ethyl acetate/hexane 2:1) and recrystallisation (ethyl acetate/hexane). (S)-2-Ethanesulfonylamino-N-(2-{4-[2-(4-fluoro-phenoxy)-ethoxy]-3-methoxy-phenyl}-ethyl)-3-methyl-butyramide is obtained, m.p. 124–125° C.

Analogously to example A1.1 the compounds listed in table A1 are obtained.

TABLE A1

| No. | $R_1$ | $R_3$ | *) | $CR_9R_{10}R_{11}$ | Data[a), b)] |
|---|---|---|---|---|---|
| A1.01 | $C_2H_5$ | $C_3H_7$-i | (S) | —$(CH_2)_2$—O—(4-F—Ph) | 124–125[a)] |
| A1.02 | $CH_3$ | $C_3H_7$-i | (S) | —$(CH_2)_2$—O—(4-F—Ph) | 124–126[a)] |
| A1.03 | $(CH_3)_2N$ | $C_3H_7$-i | (S) | —$(CH_2)_2$—O—(4-F—Ph) | 122–124[a)] |
| A1.04 | $C_2H_5$ | $C_3H_7$-n | (S) | —$(CH_2)_2$—O—(4-F—Ph) | 132–133[a)] |
| A1.05 | $C_2H_5$ | $C_2H_5$ | (S) | —$(CH_2)_2$—O—(4-F—Ph) | 113–115[a)] |
| A1.06 | $C_2H_5$ | $C_3H_7$-i | (S) | —$(CH_2)_2$—O—Ph | 112–113[a)] |
| A1.07 | $CH_3$ | $C_3H_7$-i | (S) | —$(CH_2)_2$—O—Ph | 120–123[a)] |
| A1.08 | $(CH_3)_2N$ | $C_3H_7$-i | (S) | —$(CH_2)_2$—O—Ph | 112–114[a)] |
| A1.09 | $C_2H_5$ | $C_3H_7$-n | (S) | —$(CH_2)_2$—O—Ph | 109–110[a)] |
| A1.10 | $C_2H_5$ | $C_2H_5$ | (S) | —$(CH_2)_2$—O—Ph | 131–132[a)] |
| A1.11 | $C_2H_5$ | —$CH_2$—CH=$CH_2$ | (R,S) | —$(CH_2)_2$—O—(4-F—Ph) | 115–118[a)] |
| A1.12 | $C_2H_5$ | —$CH_2$—CH=$CH_2$ | (R,S) | —$(CH_2)_2$—O—Ph | 118–119[a)] |
| A1.13 | $C_2H_5$ | $C_3H_7$-i | (S) | —$(CH_2)_2$—O—(4-Cl—Ph) | 120–122[a)] |
| A1.14 | $CH_3$ | $C_3H_7$-i | (S) | —$(CH_2)_2$—O—(4-Cl—Ph) | 122–123[a)] |
| A1.15 | $C_2H_5$ | $C_2H_5$ | (S) | —$(CH_2)_2$—O—(4-Cl—Ph) | 114–116[a)] |
| A1.16 | $C_2H_5$ | $C_3H_7$-n | (S) | —$(CH_2)_2$—O—(4-Cl—Ph) | 132–134[a)] |
| A1.17 | $CH_2$=C($CH_3$)—$CH_2$— | $C_3H_7$-i | (S) | —$(CH_2)_2$—O—(4-F—Ph) | 109–112[a)] |
| A1.18 | $C_2H_5$ | $C_4H_9$-s | (S) | —$(CH_2)_2$—O—(4-F—Ph) | 120–123[a)] |
| A1.19 | Cl—$CH_2$—$CH_2$—$CH_2$— | $C_3H_7$-i | (S) | —$(CH_2)_2$—O—(4-F—Ph) | 147–150[a)] |
| A1.20 | Cl—$CH_2$—$CH_2$—$CH_2$— | $C_3H_7$-i | (S) | —$(CH_2)_2$—O—(4-Cl—Ph) | 150–152[a)] |
| A1.21 | $C_2H_5$ | $C_3H_7$-i | (S) | —$(CH_2)_2$—O—(2-Cl—Ph) | 134–135[a)] |
| A1.22 | $C_2H_5$ | $C_3H_7$-i | (S) | —$(CH_2)_2$—O—(2-naphthyl) | 146–147[a)] |
| A1.23 | $C_2H_5$ | $C_3H_7$-i | (S) | —$(CH_2)_2$—O—(3-F—Ph) | resin, 495[c)] |
| A1.24 | $C_2H_5$ | $C_3H_7$-i | (S) | —$(CH_2)_2$—O—(4-$CH_3$—Ph) | 135–138[a)] |
| A1.25 | $C_2H_5$ | $C_3H_7$-i | (S) | —$(CH_2)_2$—O—(3-$CH_3$—Ph) | 117–118[a)] |
| A1.26 | $C_2H_5$ | $C_3H_7$-i | (S) | —$(CH_2)_2$—S—(4-Cl—Ph) | 128–129[a)] |
| A1.27 | $C_2H_5$ | $C_3H_7$-i | (S) | —$(CH_2)_2$—S—Ph | resin, 493[c)] |
| A1.28 | $CH_3$ | $C_3H_7$-i | (S) | —$(CH_2)_2$—O—(4-Br—Ph) | 543[b)] |
| A1.29 | $C_2H_5$ | $C_3H_7$-i | (S) | —$(CH_2)_2$—O—(4-Br—Ph) | 557[b)] |
| A1.30 | $C_3H_7$-n | $C_3H_7$-i | (S) | —$(CH_2)_2$—O—(4-Br—Ph) | 571[b)] |
| A1.31 | Cl—$CH_2$—$CH_2$—$CH_2$— | $C_3H_7$-i | (S) | —$(CH_2)_2$—O—(4-Br—Ph) | 605[b)] |
| A1.32 | $C_2H_5$ | $C_4H_9$-s | (S) | —$(CH_2)_2$—O—(4-Br—Ph) | 571[b)] |
| A1.33 | $C_2H_5$ | $C_2H_5$ | (S) | —$(CH_2)_2$—O—(4-Br—Ph) | 543[b)] |
| A1.34 | $C_2H_5$ | $C_3H_7$-n | (S) | —$(CH_2)_2$—O—(4-Br—Ph) | 557[b)] |
| A1.35 | $CH_3$ | $C_3H_7$-i | (S) | —$(CH_2)_2$—O—(2-Br—Ph) | 543[b)] |
| A1.36 | $C_2H_5$ | $C_3H_7$-i | (S) | —$(CH_2)_2$—O—(2-Br—Ph) | 557[b)] |
| A1.37 | $C_3H_7$-n | $C_3H_7$-i | (S) | —$(CH_2)_2$—O—(2-Br—Ph) | 571[b)] |
| A1.38 | Cl—$CH_2$—$CH_2$—$CH_2$— | $C_3H_7$-i | (S) | —$(CH_2)_2$—O—(2-Br—Ph) | 605[b)] |
| A1.39 | $C_2H_5$ | $C_4H_9$-s | (S) | —$(CH_2)_2$—O—(2-Br—Ph) | 571[b)] |
| A1.40 | $C_2H_5$ | $C_2H_5$ | (S) | —$(CH_2)_2$—O—(2-Br—Ph) | 543[b)] |
| A1.41 | $C_2H_5$ | $C_3H_7$-n | (S) | —$(CH_2)_2$—O—(2-Br—Ph) | 557[b)] |
| A1.42 | $C_3H_7$-n | $C_3H_7$-i | (S) | —$(CH_2)_2$—O—(2-Cl—Ph) | 527[b)] |
| A1.43 | $C_2H_5$ | $C_2H_5$ | (S) | —$(CH_2)_2$—O—(2-Cl—Ph) | 499[b)] |
| A1.44 | $C_2H_5$ | $C_3H_7$-n | (S) | —$(CH_2)_2$—O—(2-Cl—Ph) | 513[b)] |
| A1.45 | $CH_3$ | $C_3H_7$-i | (S) | —$(CH_2)_2$—O—(4-$CH_3$—Ph) | 479[b)] |
| A1.46 | $C_2H_5$ | $C_3H_7$-i | (S) | —$(CH_2)_2$—O—(4-$CH_3$—Ph) | 493[b)] |
| A1.47 | $C_3H_7$-n | $C_3H_7$-i | (S) | —$(CH_2)_2$—O—(4-$CH_3$—Ph) | 507[b)] |
| A1.48 | Cl—$CH_2$—$CH_2$—$CH_2$— | $C_3H_7$-i | (S) | —$(CH_2)_2$—O—(4-$CH_3$—Ph) | 541[b)] |
| A1.49 | $C_2H_5$ | $C_2H_5$ | (S) | —$(CH_2)_2$—O—(4-$CH_3$—Ph) | 479[b)] |
| A1.50 | $C_2H_5$ | $C_3H_7$-n | (S) | —$(CH_2)_2$—O—(4-$CH_3$—Ph) | 493[b)] |
| A1.51 | $C_2H_5$ | $C_3H_7$-i | (S) | —$(CH_2)_2$—O—(3-$CH_3$—Ph) | 493[b)] |
| A1.52 | $C_3H_7$-n | $C_3H_7$-i | (S) | —$(CH_2)_2$—O—(3-$CH_3$—Ph) | 507[b)] |
| A1.53 | Cl—$CH_2$—$CH_2$—$CH_2$— | $C_3H_7$-i | (S) | —$(CH_2)_2$—O—(3-$CH_3$—Ph) | 541[b)] |
| A1.54 | $C_2H_5$ | $C_4H_9$-s | (S) | —$(CH_2)_2$—O—(3-$CH_3$—Ph) | 507[b)] |
| A1.55 | $C_2H_5$ | $C_2H_5$ | (S) | —$(CH_2)_2$—O—(3-$CH_3$—Ph) | 479[b)] |
| A1.56 | $C_2H_5$ | $C_3H_7$-n | (S) | —$(CH_2)_2$—O—(3-$CH_3$—Ph) | 493[b)] |
| A1.57 | $C_2H_5$ | $C_3H_7$-i | (S) | —$(CH_2)_2$—O—(3-F—Ph) | 497[b)] |
| A1.58 | $C_3H_7$-n | $C_3H_7$-i | (S) | —$(CH_2)_2$—O—(3-F—Ph) | 511[b)] |
| A1.59 | $C_2H_5$ | $C_2H_5$ | (S) | —$(CH_2)_2$—O—(3-F—Ph) | 483[b)] |
| A1.60 | $C_2H_5$ | $C_3H_7$-n | (S) | —$(CH_2)_2$—O—(3-F—Ph) | 497[b)] |
| A1.61 | $C_3H_7$-n | $C_3H_7$-i | (S) | —$(CH_2)_2$—O—(3,4-$Cl_2$—Ph) | 561[b)] |
| A1.62 | Cl—$CH_2$—$CH_2$—$CH_2$— | $C_3H_7$-i | (S) | —$(CH_2)_2$—O—(3,4-$Cl_2$—Ph) | 595[b)] |
| A1.63 | $C_2H_5$ | $C_4H_9$-s | (S) | —$(CH_2)_2$—O—(3,4-$Cl_2$—Ph) | 561[b)] |
| A1.64 | $C_2H_5$ | $C_2H_5$ | (S) | —$(CH_2)_2$—O—(3,4-$Cl_2$—Ph) | 533[b)] |
| A1.65 | $C_2H_5$ | $C_3H_7$-n | (S) | —$(CH_2)_2$—O—(3,4-$Cl_2$—Ph) | 547[b)] |
| A1.66 | $C_2H_5$ | $C_3H_7$-i | (S) | —$(CH_2)_2$—O—(2-naphthyl) | 529[b)] |
| A1.67 | $C_3H_7$-n | $C_3H_7$-i | (S) | —$(CH_2)_2$—O—(2-naphthyl) | 543[b)] |
| A1.68 | $C_2H_5$ | $C_4H_9$-s | (S) | —$(CH_2)_2$—O—(2-naphthyl) | 543[b)] |

TABLE A1-continued

| No. | $R_1$ | $R_3$ | *) | $CR_9R_{10}R_{11}$ | Data[a), b)] |
|---|---|---|---|---|---|
| A1.69 | $C_2H_5$ | $C_2H_5$ | (S) | —$(CH_2)_2$—O—(2-naphthyl) | 515[b)] |
| A1.70 | $C_2H_5$ | $C_3H_7$-i | (S) | —$(CH_2)_2$—N$(C_2H_5)$—Ph | 108–110[a)] |
| A1.71 | $C_2H_5$ | $C_3H_7$-i | (S) | —$(CH_2)_2$—N$(CH_3)$—Ph | 106–107[a)] |
| A1.72 | $C_2H_5$ | $C_3H_7$-i | (S) | —$CH(CH_3)$—$CH_2$—O—(4-Cl—Ph) | resin, 525[c)] |
| A1.73 | $CH_3$ | $C_3H_7$-i | (S) | —$(CH_2)_2$—O—(2-Cl—Ph) | 132–133[a)] |
| A1.74 | $CH_3$ | $C_3H_7$-i | (S) | —$(CH_2)_2$—O—(2-naphthyl) | 147–148[a)] |
| A1.75 | $CH_3$ | $C_3H_7$-i | (S) | —$(CH_2)_2$—O—(3,4-$Cl_2$—Ph) | 143–144[a)] |
| A1.76 | $CH_3$ | $C_3H_7$-i | (S) | —$(CH_2)_2$—O—(3-F—Ph) | 113–115[a)] |
| A1.77 | $CH_3$ | $C_3H_7$-i | (S) | —$(CH_2)_2$—O—(3-$CH_3$—Ph) | 116–117[a)] |
| A1.78 | $CH_3$ | $C_3H_7$-i | (S) | —$(CH_2)_2$—S—(4-Cl—Ph) | resin, 513[c)] |
| A1.79 | $CH_3$ | $C_3H_7$-i | (S) | —$(CH_2)_2$—N$(C_2H_5)$—Ph | 121–122[a)] |
| A1.80 | $CH_3$ | $C_3H_7$-i | (S) | —$CH(CH_3)$—$CH_2$—O—(4-Cl—Ph) | 109–110[a)] |
| A1.81 | $CH_3$ | $C_3H_7$-i | (S) | —$(CH_2)_2$—N$(CH_3)$—Ph | 128–129[a)] |
| A1.82 | $(CH_3)_2N$ | $C_3H_7$-i | (S) | —$(CH_2)_2$—O—(2-Cl—Ph) | 97–100[a)] |
| A1.83 | $C_2H_5$ | $C_3H_7$-i | (S) | —$(CH_2)_2$—O—(3,4-$Cl_2$—Ph) | 129–130[a)] |
| A1.84 | $CH_3$ | $C_3H_7$-i | (S) | —$(CH_2)_2$—S—Ph | 124–126[a)] |
| A1.85 | $(CH_3)_2N$ | $C_3H_7$-i | (S) | —$(CH_2)_2$—O—(2-naphthyl) | 149–150[a)] |
| A1.86 | $(CH_3)_2N$ | $C_3H_7$-i | (S) | —$(CH_2)_2$—O—(3-F—Ph) | 106–109[a)] |
| A1.87 | $(CH_3)_2N$ | $C_3H_7$-i | (S) | —$(CH_2)_2$—O—(4-$CH_3$—Ph) | 508[b)] |
| A1.88 | $(CH_3)_2N$ | $C_3H_7$-i | (S) | —$(CH_2)_2$—O—(3-$CH_3$—Ph) | 115–117[a)] |
| A1.89 | $(CH_3)_2N$ | $C_3H_7$-i | (S) | —$(CH_2)_2$—S—(4-Cl—Ph) | 139–141[a)] |
| A1.90 | $(CH_3)_2N$ | $C_3H_7$-i | (S) | —$(CH_2)_2$—S—Ph | 106–107[a)] |
| A1.91 | $(CH_3)_2N$ | $C_3H_7$-i | (S) | —$(CH_2)_2$—N$(C_2H_5)$—Ph | 521[b)] |
| A1.92 | $(CH_3)_2N$ | $C_3H_7$-i | (S) | —$CH(CH_3)$—$CH_2$—O—(4-Cl—Ph) | 542[b)] |
| A1.93 | Cl—$CH_2$—$CH_2$—$CH_2$— | $C_3H_7$-i | (S) | —$(CH_2)_2$—O—(2-Cl—Ph) | 161–162[a)] |
| A1.94 | Cl—$CH_2$—$CH_2$—$CH_2$— | $C_3H_7$-i | (S) | —$(CH_2)_2$—O—(2-naphthyl) | 181–183[a)] |
| A1.95 | Cl—$CH_2$—$CH_2$—$CH_2$— | $C_3H_7$-i | (S) | —$(CH_2)_2$—O—(3-F—Ph) | resin, 543[c)] |
| A1.96 | Cl—$CH_2$—$CH_2$—$CH_2$— | $C_3H_7$-i | (S) | —$(CH_2)_2$—S—(4-Cl—Ph) | 575[b)] |
| A1.97 | Cl—$CH_2$—$CH_2$—$CH_2$— | $C_3H_7$-i | (S) | —$(CH_2)_2$—S—Ph | resin, 541[c)] |
| A1.98 | Cl—$CH_2$—$CH_2$—$CH_2$— | $C_3H_7$-i | (S) | —$(CH_2)_2$—N$(C_2H_5)$—Ph | 554[b)] |
| A1.99 | Cl—$CH_2$—$CH_2$—$CH_2$— | $C_3H_7$-i | (S) | —$CH(CH_3)$—$CH_2$—O—(4-Cl—Ph) | 105–107[a)] |
| A1.100 | $C_2H_5$ | $C_4H_9$-s | (S) | —$(CH_2)_2$—O—(2-Cl—Ph) | 123–124[a)] |
| A1.101 | $C_2H_5$ | $C_4H_9$-s | (S) | —$(CH_2)_2$—O—(3-F—Ph) | 124–126[a)] |
| A1.102 | $C_2H_5$ | $C_4H_9$-s | (S) | —$(CH_2)_2$—O—(4-$CH_3$—Ph) | 136–137[a)] |
| A1.103 | $C_2H_5$ | $C_4H_9$-s | (S) | —$(CH_2)_2$—N$(C_2H_5)$—Ph | 520[b)] |
| A1.104 | $C_2H_5$ | $C_4H_9$-s | (S) | —$CH(CH_3)$—$CH_2$—O—(4-Cl—Ph) | resin, 539[c)] |
| A1.105 | $C_2H_5$ | $C_3H_7$-n | (S) | —$CH_2$—CH=CH—(4-Cl—Ph) | 139–140[a)] |
| A1.106 | $C_2H_5$ | $C_4H_9$-s | (S) | —$CH_2$—CH=CH—(4-Cl—Ph) | 143–145[a)] |
| A1.107 | $C_2H_5$ | $C_3H_5$-c | (S) | —$CH_2$—CH=CH—(4-Cl—Ph) | 135–136[a)] |
| A1.108 | $C_2H_5$ | $CH_2$—C≡CH | (R,S) | —$CH_2$—CH=CH—(4-Cl—Ph) | 142–143[a)] |
| A1.109 | $C_2H_5$ | $C_2H_5$ | (S) | —$CH_2$—CH=CH—(4-Cl—Ph) | 125–127[a)] |
| A1.110 | $C_2H_5$ | CH(OH)—$CH_3$ | (S) | —$CH_2$—CH=CH—(4-Cl—Ph) | 139–141[a)] |

[a)] m.p. (° C.),
[b)] mass spectra m/e (M[+] + 1),
[c)] mass spectra m/e (M[+] − 1),
*) Configuration on the α-C-atom in the amino acid moiety
Ph means phenyl

A1.111 m.p. 134–136° C

EXAMPLE A2.1.

E-(S)-2-Ethanesulfonylamino-N-{2-[3-methoxy-4-(3-phenyl-allyloxy)-phenyl]-ethyl}-3-methyl-butyramide

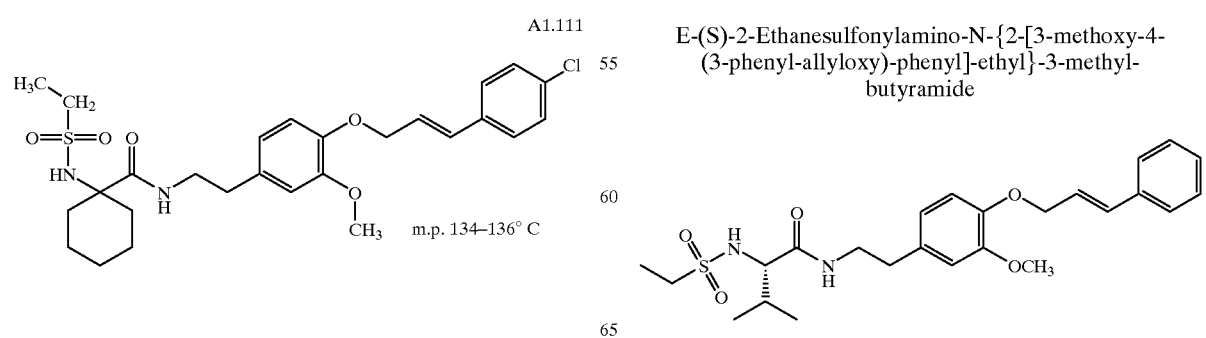

A mixture of (S)-N-[2-(4-hydroxy-3-methoxy-phenyl)-ethyl]-2-methanesulfonylamino-3-methyl-butyramide (2.5 g), E-(3-bromo-propenyl)-benzene(1.5 g) and sodium methoxide (9 ml 1M solution in methanol) in methanol (30 ml) is heated to reflux for 4 hours. Upon cooling water (400 ml) is added. The mixture is extracted with ethyl acetate (2×300 ml). The organic layers are washed with brine (100 ml), dried (MgSO$_4$) and evaporated. The resulting residue is purified by recrystallisation (ethyl acetate/hexane). E-(S)-2-Ethanesulfonylamino-N-{2-[3-methoxy-4-(3-phenyl-allyloxy)-phenyl]-ethyl}-3-methyl-butyramide is obtained, m.p. 128–133° C.

Analogously to example A2.1 the compounds listed in table A2 are obtained.

TABLE A2

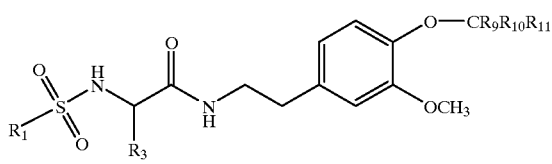

| No. | $R_1$ | $R_3$ | *) | A | Data[a), b)] |
|---|---|---|---|---|---|
| A2.01 | $C_2H_5$ | $C_3H_7$-i | (S) | Ph | 128–133[a)] |
| A2.02 | $CH_3$ | $C_3H_7$-i | (S) | Ph | Oil, 510[b)] |
| A2.03 | $C_2H_5$ | $C_3H_7$-i | (S) | 4-Cl—Ph | 147–149[a)] |
| A2.04 | $CH_3$ | $C_3H_7$-i | (S) | 4-Cl—Ph | 144–149[a)] |
| A2.05 | $(CH_3)_2N$ | $C_3H_7$-i | (S) | 4-Cl—Ph | 79–82[a)] |
| A2.06 | $C_2H_5$ | $C_3H_7$-i | (S) | 3-$CF_3$—Ph | resin, 541[c)] |
| A2.07 | $CH_3$ | $C_3H_7$-i | (S) | 3-$CF_3$—Ph | 113–114[a)] |
| A2.08 | $(CH_3)_2N$ | $C_3H_7$-i | (S) | 3-$CF_3$—Ph | 105–107[a)] |
| A2.09 | $C_2H_5$ | $C_3H_7$-i | (S) | 2-F—Ph | 146–148[a)] |
| A2.10 | $CH_3$ | $C_3H_7$-i | (S) | 2-F—Ph | resin, 479[b)] |
| A2.11 | $(CH_3)_2N$ | $C_3H_7$-i | (S) | 2-F—Ph | 112–114[a)] |
| A2.12 | $C_2H_5$ | $C_3H_7$-i | (S) | 3,4-$Cl_2$—Ph | 126–128[a)] |
| A2.13 | $CH_3$ | $C_3H_7$-i | (S) | 3,4-$Cl_2$—Ph | 133–135[a)] |
| A2.14 | $C_2H_5$ | $C_3H_7$-i | (S) | 4-Br—Ph | 153–155[a)] |
| A2.15 | $(CH_3)_2N$ | $C_3H_7$-i | (S) | 4-Br—Ph | 96–98[a)] |
| A2.16 | $CH_3$ | $C_3H_7$-i | (S) | 4-Br—Ph | 159–162[a)] |
| A2.17 | $(CH_3)_2N$ | $C_3H_7$-i | (S) | 3,4-$Cl_2$—Ph | 129–131[a)] |
| A2.18 | $C_2H_5$ | $C_3H_7$-i | (S) | 1-naphthyl | 99–102[a)] |
| A2.19 | $CH_3$ | $C_3H_7$-i | (S) | 1-naphthyl | 123–125[a)] |

[a)]m.p. (° C.),
[b)]mass spectra m/e (M$^+$ + 1),
[c)]mass spectra m/e (M$^+$ − 1)
*)Configuration on the α-C-atom in the amino acid moiety
Ph means phenyl In analogy to Example A2.1 the compounds of the following Table are obtained

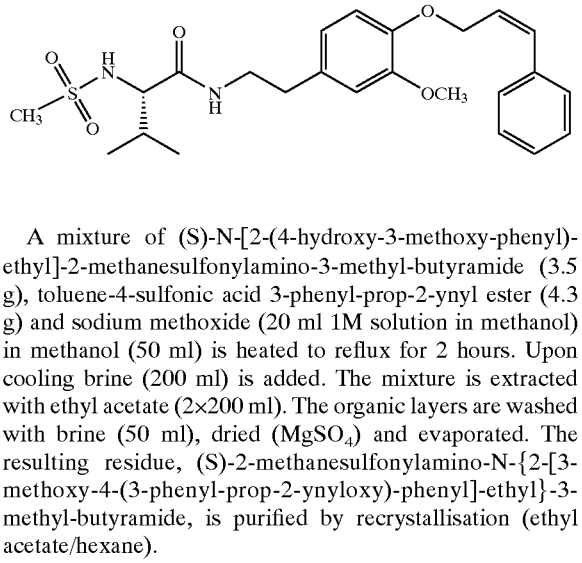

| No | $R_1$ | $R_3$ | *) | $CR_9R_{10}R_{11}$ | Data |
|---|---|---|---|---|---|
| A2.100 | $C_2H_5$ | $C_3H_7$-i | (S) | —$(CH_2)_2$—NH-Ph | Oil $^1$H-NMR (CDCl$_3$) δ (ppm): 0.89 (d, 3H); 0.95 (d, 3H); 1.32 (t, 3H); 1.9–2.15 (m, 1H); 2.75 (t, 2H); 2.98 (q, 2H); 3.25–3.35 (m, 2H); 3.45–3.6 (m, 3H); 3.8–3.9 (m, 5H); 5.20 (d, 1H); 6.09 (t, 1H); 6.65–6.85 (m, 6H); 7.1–7.3 (m, 2H) |
| A2.101 | $C_2H_5$ | $C_3H_7$-i | (S) | —$(CH_2)_2$—NH-Ph | Oil $^1$H-NMR (CDCl$_3$) δ (ppm): 0.89 (d, 3H); 0.99 (d, 3H); 1.8–1.95 (m, 1H); 2.6–2.8 (m, 2H); 2.96 (s, 3H); 3.02 (s, 3H); 3.15–3.35 (m, 4H); 3.8–3.9 (m, 5H); 3.96 (dd, 1H); 4.25 (t, 3H); 5.45 (d, 1H); 6.6–6.9 (m, 6H); 7.1–7.25 (m, 2H) |

EXAMPLE A3.1

Z-(S)-2-Methanesulfonylamino-N-{2-[3-methoxy-4-(3-phenyl-allyloxy)-phenyl]-ethyl}-3-methyl-butyramide A mixture of (S)-N-[2-(4-hydroxy-3-methoxy-phenyl)-ethyl]-2-methanesulfonylamino-3-methyl-butyramide (3.5 g), toluene-4-sulfonic acid 3-phenyl-prop-2-ynyl ester (4.3 g) and sodium methoxide (20 ml 1M solution in methanol) in methanol (50 ml) is heated to reflux for 2 hours. Upon cooling brine (200 ml) is added. The mixture is extracted with ethyl acetate (2×200 ml). The organic layers are washed with brine (50 ml), dried (MgSO$_4$) and evaporated. The resulting residue, (S)-2-methanesulfonylamino-N-{2-[3-methoxy-4-(3-phenyl-prop-2-ynyloxy)-phenyl]-ethyl}-3-methyl-butyramide, is purified by recrystallisation (ethyl acetate/hexane).

This compound (1.7 g) is dissolved in tetrahyrofuran (40 ml), Lindlar-catalyst (5%-Pd on CaSO$_4$; 340 mg), 3,6-dithia-1,8-octandiol (4 mg) and 2,2'-(ethylenedithio)-diethanol (4 mg) are added. The resulting mixture is shaken under a hydrogen atmosphere at room temperature and at normal pressure for 24 h. It is then filtered and evaporated.

Z-(S)-2-Methanesulfonylamino-.N.-{2-[3-methoxy-4-(3-phenyl-allyloxy)-phenyl]-ethyl}-3-methyl-butyramide is obtained, oil.

Analogously to example A3.1 the compounds listed in table A3 are obtained.

TABLE A3

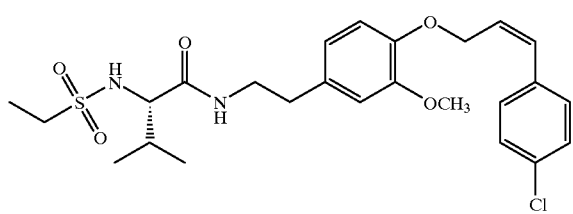

| No. | $R_1$ | $R_3$ | *) | A | Data |
|---|---|---|---|---|---|
| A3.01 | $CH_3$ | $C_3H_7$-i | (S) | Ph | Oil, 461[b)] |
| A3.02 | $C_2H_5$ | $C_3H_7$-i | (S) | Ph | Oil, 475[b)] |
| A3.03 | $C_2H_5$ | $C_3H_7$-i | (S) | 4-Cl—Ph | 141–143[a)] |

[a)] m.p. (° C.),
[b)] mass spectra m/e ($M^+$ + 1)
*) Configuration on the α-C-atom in the amino acid moiety
Ph means phenyl

EXAMPLE A3.2

Z-(S)-N-(2-{4-[3-(4-Chloro-phenyl)-allyloxy]-3-methoxy-phenyl}-ethyl)-2-ethanesulfonylamino-3-methyl-butyramide To a mixture of BOC-L-Valin (48 g), 4-(2-Amino-ethyl)-2-methbxy-phenol hydrochloride (45 g) and diethyl-isopropylamine (64.6 g) in dimethylformamide (900 ml) is added benzotriazol-1-yloxy-tris(dimethylamino) phosphonium hexafluorophosphate (97.8 g) in one portion. The reaction mixture is stirred for 4 hours at room temperature. Water (1000 ml) is then added. The mixture is extracted with ethyl acetate (2×500 ml). The organic layers organic layers are washed with brine (2×400 ml), dried ($MgSO_4$) and evaporated. The residue is purified by flash column chromatography on silica gel (ethyl acetate/hexane 1:2). (S)-{1-[2-(4-Hydroxy-3-methoxy-phenyl)-ethylcarbamoyl]-2-methyl-propyl}-carbamic acid tert.-butyl ester is obtained.

A mixture of (S)-{1-[2-(4-hydroxy-3-methoxy-phenyl)-ethylcarbamoyl]-2-methyl-propyl}-carbamic acid -tert.-butyl ester (36.6 g) toluene-4-sulfonic acid 3-(4-chloro-phenyl)-prop-2-ynyl ester (50 g), sodium iodide (20 mg) and sodium methoxide (200 ml 1M solution in methanol) in methanol (300 ml) is heated to reflux for 2 hours. Upon cooling brine (1500 ml) is added. the mixture is extracted with ethyl acetate (2×700 ml). The organic layers are washed with brine (200 ml), dried ($MgSO_4$) and evaporated. The resulting residue is purified by flash column chromatography on silica gel (ethyl acetate/hexane 1:2) and recrystallised (ethyl acetate/hexane). (S)-[1-(2-{4-[3-(4-Chloro-phenyl)-prop-2-ynyloxy]-3-methoxy-phenyl}-ethylcarbamoyl)-2-methyl-propyl]-carbamic acid-tert.-butyl ester is obtained.

To (S)-[1-(2-{4-[3-(4-chloro-phenyl)-prop-2-ynyloxy]-3-methoxy-phenyl}ethylcarbamoyl)-2-methyl-propyl]-carbamic acid-tert.-butyl ester (18 g) in tetrahyrofuran (180 ml), Lindlar-catalyst (5%-Pd on $CaSO_4$; 7.2 g), 3,6-dithia-1,8-octandiol (45 mg) and 2,2'-(ethylenedithio)-diethanol (45 mg) are added. The resulting mixture is shaken under a hydrogen atmosphere at room temperature and at normal pressure for 5 hours. It is then filtered and evaporated. The residue is purified by flash column chromatography on silica gel (ethyl acetate/hexane 1:2) and recrystallised (ethyl acetate/hexane). Z-(S)-[1-(2-{4-[3-(4-Chloro-phenyl)-allyloxy]-3-methoxy-phenyl}-ethylcarbamoyl)-2-methyl-propyl]-carbamic acid-tert.-butyl ester is obtained, m.p. 82–84° C.

To concentrated hydrochloric acid (2.7 g; precooled to 0° C.) is added. Z-(S)-[1-(2-{4-[3-(4-chloro-phenyl)-allyloxy]-3-methoxy-phenyl}-ethylcarbamoyl)-2-methyl-propyl]-carbamic acid -tert.-butyl ester (3 g) in dichloromethane (20 ml). The resulting mixture is vigorously stirred for 16 hours at room temperature. The mixture is adjusted to pH 12 by adding 2N sodium hydroxide. It is then extracted with dichloromethane (2×100 ml). The organic layers are washed with brine (100 ml), dried ($K_2CO_3$) and evaporated. Z-(S)-2-Amino-.N.-(2-{4-[3-(4-chloro-phenyl)-allyloxy]-3-methoxy-phenyl}-ethyl)-3-methyl-butyramide is obtained.

To Z-(S)-2-amino-N-(2-{4-[3-(4-chloro-phenyl)-allyloxy]-3-methoxy-phenyl}-ethyl)-3-methyl-butyramide (1.7 g), and triethylamine (1 g) in dioxane (30 ml) is added ethane sulfochloride (0.52 g). The mixture is stirred at room temperature for 16 hours. Brine (200 ml) is added. It is extracted with ethyl acetate (2×200 ml). The organic layers are washed with brine (100 ml) dried and evaporated. The residue is purified by flash column chromatography on silica gel (ethyl acetate/hexane 1:1) and recrystallised. Z-(S)-N-(2-{4-[3-(4-Chloro-phenyl)-allyloxy]-3-methoxy-phenyl}-ethyl)-2-ethanesulfonylamino-3-methyl-butyramide is obtained, m.p. 141–143° C.

EXAMPLE B1.1

{4-[2-(4-Fluoro-phenoxy)-ethoxy]-3-methoxy-phenyl}-acetonitrile

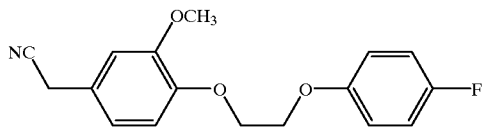

A mixture of 4-hydroxy-3-methoxy-benzyl alcohol (14.7 g) and sodium cyanide (5 g) in dimethylformamide (200 ml) is stirred under an atmosphere of nitrogen for 3 hours at +120° C. The mixture is then cooled to +100° C. and 1-(2-bromo-ethoxy)-4-fluoro-benzene (25 g) is added in one portion. The mixture is stirred at +100° C. for another 4 hours. Upon cooling water (800 ml) is added. The mixture is extracted with ethyl acetate (2×500 ml). The organic phases are washed with brine (2×500 ml), dried ($MgSO_4$) and evaporated. The residue is recrystallised from ethyl acetate/hexane. {4-[2-(4-Fluoro-phenoxy)-ethoxy]-3-methoxy-phenyl}-acetonitrile is obtained, m.p. 126–128° C.

Analogously to example B1.1 the compounds listed in table B1 are obtained.

Ph means phenyl

TABLE B1

Structure: NC-CH2-[3-OCH3, 4-O-CR9R10R11-phenyl]

| No | CR9R10R11 | Data |
|---|---|---|
| B1.01 | —(CH$_2$)$_2$—O—(4-F—Ph) | 126–128[a] |
| B1.02 | —(CH$_2$)$_2$—O—Ph | 108–109[a] |
| B1.03 | —(CH$_2$)$_2$—O—(4-Cl—Ph) | 137–139[a] |
| B1.04 | —(CH$_2$)$_2$—O—(2-Cl—Ph) | 93–95[a] |
| B1.05 | —(CH$_2$)$_2$—O—(2-naphthyl) | 106–111[a] |
| B1.06 | —(CH$_2$)$_2$—O—(3-F—Ph) | 90–92[a] |
| B1.07 | —(CH$_2$)$_2$—O—(4-CH$_3$—Ph) | 100–102[a] |
| B1.08 | —(CH$_2$)$_2$—O—(3-CH$_3$—Ph) | 104–106[a] |
| B1.09 | —(CH$_2$)$_2$—O—(3,4-Cl$_2$—Ph) | 107–110[a] |
| B1.10 | —(CH$_2$)$_2$—O—(4-Br—Ph) | 136–141[a] |
| B1.11 | —(CH$_2$)$_2$—O—(2-Br—Ph) | 99–108[a] |
| B1.12 | —CH(CH$_3$)—CH$_2$—O—(4-Cl—Ph) | Oil, $^1$H-NMR (CDCl$_3$) δ (ppm): 1.45(d, 3H); 3.70(s, 2H); 3.84(s, 3H); 3.95–4.2(m, 2H); 4.6–4.7(m, 1H); 6.8–7.0 (m, 5H); 7.2–7.25(m, 2H) |
| B1.13 | —(CH$_2$)$_2$—S—Ph | Oil, $^1$H-NMR (CDCl$_3$) δ (ppm): 3.32(t, 2H); 3.67(s, 2H); 3.86(s,3H); 4.17(t, 2H); 6.7–6.8(m, 3H); 7.15–7.45(m, 5H) |
| B1.14 | —(CH$_2$)$_2$—S—(4-Cl—Ph) | 91–93[a] |
| B1.15 | —(CH$_2$)$_2$—N(CH$_3$)—Ph | Oil, 297[b] |
| B1.16 | —(CH$_2$)$_2$—N(C$_2$H$_5$)—Ph | Oil, $^1$H-NMR (CDCl$_3$) δ (ppm): 1.19(t, 3H); 3.46(q, 2H); 3.68(s, 2H); 3.77(t, 2H); 3.88(s, 3H); 4.14(t, 2H); 6.6–6.85(m, 6H); 7.2–7.3(m, 2H) |

[a] m.p. (° C.),
[b] mass spectra m/e (M$^+$ + 1)

EXAMPLE B2.1

2-{4-[2-(4-Fluoro-phenoxy]-ethoxyl-3-methoxy-phenyl}-ethylamine

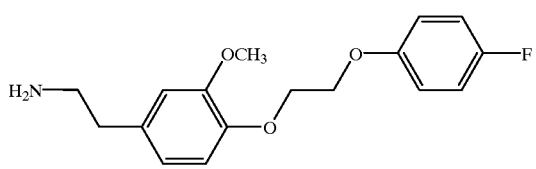

A mixture of {4-[2-(4-fluoro-phenoxy)-ethoxy]-3-methoxy-phenyl}-acetonitrile (14.8 g), liquid ammonia (8.4 g) and Raney-nickel (4.5 g) in tetrahydrofuran (120 ml) is shaken in an autoclave under hydrogen (130 bar) at +60° C. for 2 hours. The reaction mixture is filtered and evaporated. 2-{4-[2-(4-Fluoro-phenoxy)-ethoxy]-3-methoxy-phenyl}-ethylamine is obtained as an oil.

Analogously to example B2.1 the compounds listed in table B2 are obtained.

TABLE B2

Structure: H2N-CH2CH2-[3-OCH3, 4-O-CR9R10R11-phenyl]

| No | CR9R10R11 | Data |
|---|---|---|
| B2.01 | —(CH$_2$)$_2$—O—(4-F—Ph) | oil, $^1$H-NMR(CDCl$_3$) δ (ppm): 1.60(s, 2H); 2.75(t, 2H); 3.00(t, 2H); 3.85(s, 3H); 4.25–4.35(m, 4H); 6.7–7.1 (m, 7H) |
| B2.02 | —(CH$_2$)$_2$—O—Ph | oil, $^1$H—NMR(CDCl$_3$) δ (ppm): 1.59(s, 2H); 2.73(t, 2H); 3.00(t, 2H); 3.85(s, 3H); 4.3–4.35(m, 4H); 6.7–6.75(m, 2H); 6.85–7.0(m, 4H); 7.2–7.35(m, 2H) |
| B2.03 | —(CH$_2$)$_2$—O—(4-Cl—Ph) | oil, $^1$H-NMR(CDCl$_3$) δ (ppm): 1.50(s, 2H); 2.69 (t, 2H); 2.94(t, 2H); 3.84(s, 3H); 4.3–4.35(m, 4H); 6.7–6.9(m, 5H); 7.15–7.3 (m, 2H) |
| B2.04 | —(CH$_2$)$_2$—O—(2-Cl—Ph) | 69–71[a] |
| B2.05 | —(CH$_2$)$_2$—O—(2-naphthyl) | oil, 338[b] |
| B2.06 | —(CH$_2$)$_2$—O—(3-F—Ph) | oil, 306[b] |
| B2.07 | —(CH$_2$)$_2$—O—(4-CH$_3$—Ph) | resin, $^1$H-NMR(CDCl$_3$) δ (ppm): 1.31(s, 2H); 2.28 (s, 3H); 2.69(t, 2H); 2.95(t, 2H); 3.85(s, 3H); 4.25–4.4(m, 4H); 6.7–6.95(m, 5H); 7.05–7.1(m, 2H) |
| B2.08 | —(CH$_2$)$_2$—O—(3-CH$_3$—Ph) | resin, 302[b] |
| B2.09 | —(CH$_2$)$_2$—O—(3,4-Cl$_2$—Ph) | resin, $^1$H-NMR(CDCl$_3$) δ (ppm): 1.22(s, 2H); 2.69 (t, 2H); 2.95(t, 2H); 3.84(s, 3H); 4.2–4.4(m, 4H); 6.7–7.3(m, 6H); |
| B2.10 | —(CH$_2$)$_2$—O—(4-Br—Ph) | resin, 366[b] |
| B2.11 | —(CH$_2$)$_2$—O—(2-Br—Ph) | oil, 366[b] |
| B2.12 | —CH(CH$_3$)—CH$_2$—O—(4-Cl—Ph) | oil, 336[b] |
| B2.13 | —(CH$_2$)$_2$—S—Ph | oil, 304[b] |
| B2.14 | —(CH$_2$)$_2$—S—(4-Cl—Ph) | 338[b] |
| B2.15 | —(CH$_2$)$_2$—N(CH$_3$)—Ph | oil, 301[b] |
| B2.16 | —(CH$_2$)$_2$—N(C$_2$H$_5$)—Ph | oil, 315[b] |

[a] m.p.(° C.),
[b] mass spectra m/e (M$^+$ + 1),
Ph means phenyl

To 2-{4-[2-(4-fluoro-phenoxy)-ethoxy]-3-methoxy-phenyl}-ethylamine (15.7 g) dissolved in diethylether (200 ml) is added 1M hydrogen chloride solution in diethylether (75 ml). The resulting residue is isolated by separation in a centrifuge and decantation. 2-{4-[2-(4-Fluoro-phenoxy)-ethoxy]-3-methoxy-phenyl}-ethylamine hydrochloride is obtained.

EXAMPLE C1.1

[3-Methoxy-4-(3-phenyl-prop-2-ynyloxy)-phenyl]-acetonitrile

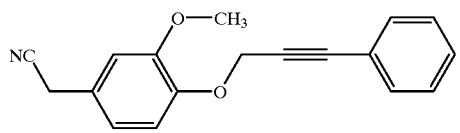

A mixture of (4-hydroxy-3-methoxy-phenyl)-acetonitrile (17.4 g) and sodium cyanide (6.6 g) in dimethylformamide (250 ml) is stirred under an atmosphere of nitrogen for 3 hours at +120° C. The mixture is then cooled to +60° C. and toluene-4-sulfonic acid 3-phenyl-prop-2-ynyl ester (39 g) in dimethylformamid (50 ml)is added during 5 minutes. It is stirred at +65° C. for another 4 hours. Upon cooling water (800 ml) is added. The mixture is extracted with ethyl acetate (2×500 ml). The organic phases are washed with brine (2×500 ml), dried ($MgSO_4$) and evaporated. The residue is purified by flash column chromatography on silica gel (ethyl acetate/hexane 1:3) and recrystallised from ethyl acetate/hexane. [3-Methoxy-4-(3-phenyl-prop-2-ynyloxy)-phenyl]-acetonitrile is obtained, m.p. 74–75° C.

Analogously to example C1.1 the compounds listed in table C1 are obtained.

Ph means phenyl

TABLE C1

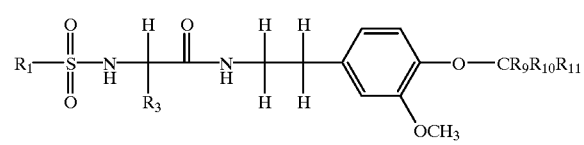

| No | A | m.p. (° C.) |
|---|---|---|
| C1.01 | Ph | 74–75 |
| C1.02 | 4-Cl—Ph | 108—109 |
| C1.03 | 4-F—Ph | oil |

Analogously to the above Examples the following compounds of Tables 1 to 37 may be prepared. In the tables Ph means phenyl.

Table 1: Compounds represented by the Formula I.1 wherein the combination of the groups $R_1$, $R_3$, $R_9$, $R_{10}$ and $R_{11}$ corresponds to each row in table A.

I.1

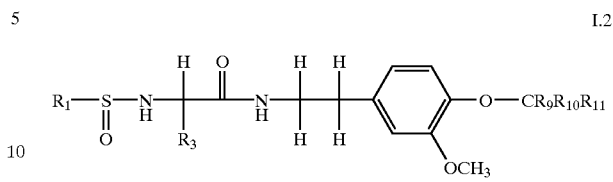

Table 2: Compounds represented by the Formula I.2 wherein the combination of the groups $R_1$, $R_3$, $R_9$, $R_{10}$ and $R_{11}$ corresponds to each row in table A.

I.2

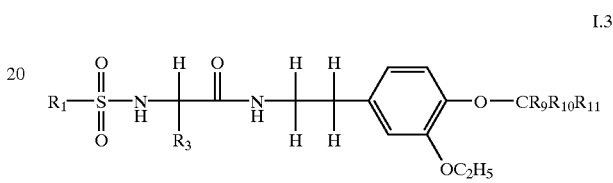

Table 3: Compounds represented by the Formula I.3 wherein the combination of the groups $R_1$, $R_3$, $R_9$, $R_{10}$ and $R_{11}$ corresponds to each row in table A.

I.3

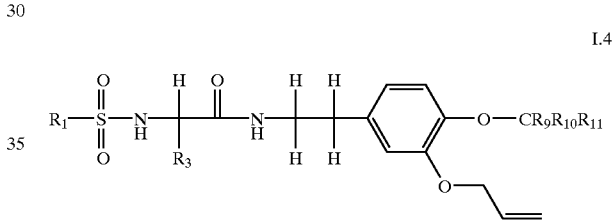

Table 4: Compounds represented by the Formula I.4 wherein the combination of the groups $R_1$, $R_3$, $R_9$, $R_{10}$ and $R_{11}$ corresponds to each row in table A.

I.4

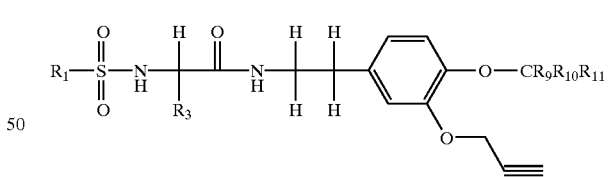

Table 5: Compounds represented by the Formula I.5 wherein the combination of the groups $R_1$, $R_3$, $R_9$, $R_{10}$ and $R_{11}$ corresponds to each row in table A.

I.5

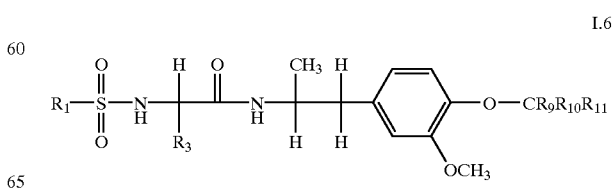

Table 6: Compounds represented by the Formula I.6 wherein the combination of the groups $R_1$, $R_3$, $R_9$, $R_{10}$ and $R_{11}$ corresponds to each row in table A.

I.6

Table 7: Compounds represented by the Formula I.7 wherein the combination of the groups $R_1$, $R_3$, $R_9$, $R_{10}$ and $R_{11}$ corresponds to each row in table A.

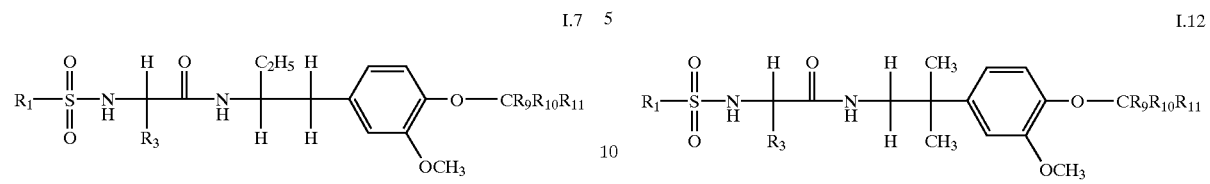

I.7

Table 8: Compounds represented by the Formula I.8 wherein the combination of the groups $R_1$, $R_3$, $R_9$, $R_{10}$ and $R_{11}$ corresponds to each row in table A.

I.8

Table 9: Compounds represented by the Formula I.9 wherein the combination of the groups $R_1$, $R_3$, $R_9$, $R_{10}$ and $R_{11}$ corresponds to each row in table A.

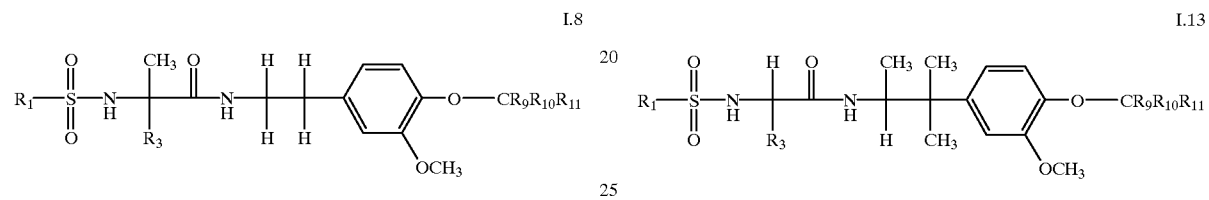

I.9

Table 10: Compounds represented by the Formula I.10 wherein the combination of the groups $R_1$, $R_3$, $R_9$, $R_{10}$ and $R_{11}$ corresponds to each row in table A.

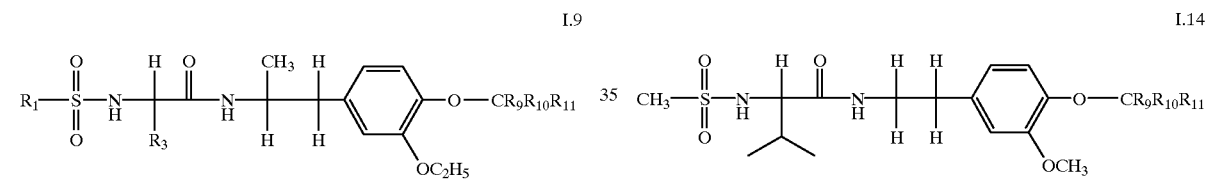

I.10

Table 11: Compounds represented by the Formula I.11 wherein the combination of the groups $R_1$, $R_3$, $R_9$, $R_{10}$ and $R_{11}$ corresponds to each row in table A.

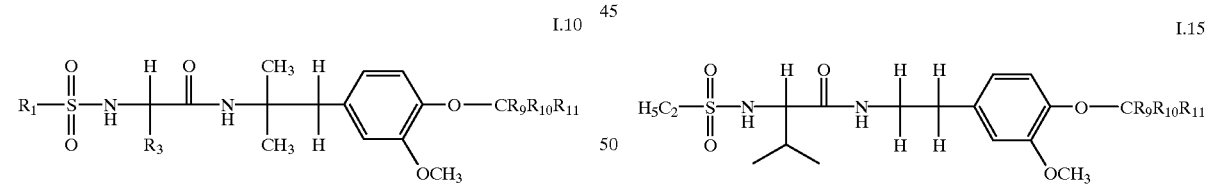

I.11

Table 12: Compounds represented by the Formula I.12 wherein the combination of the groups $R_1$, $R_3$, $R_9$, $R_{10}$ and $R_{11}$ corresponds to each row in table A.

I.12

Table 13: Compounds represented by the Formula I.13 wherein the combination of the groups $R_1$, $R_3$, $R_9$, $R_{10}$ and $R_{11}$ corresponds to each row in table A.

I.13

Table 14: Compounds represented by the Formula I.14 wherein the combination of the groups $R_9$, $R_{10}$ and $R_{11}$ corresponds to each row in table B.

I.14

Table 15: Compounds represented by the Formula I.15 wherein the combination of the groups $R_9$, $R_{10}$ and $R_{11}$ corresponds to each row in table B.

I.15

Table 16: Compounds represented by the Formula I.16 wherein the combination of the groups $R_9$, $R_{10}$ and $R_{11}$ corresponds to each row in table B.

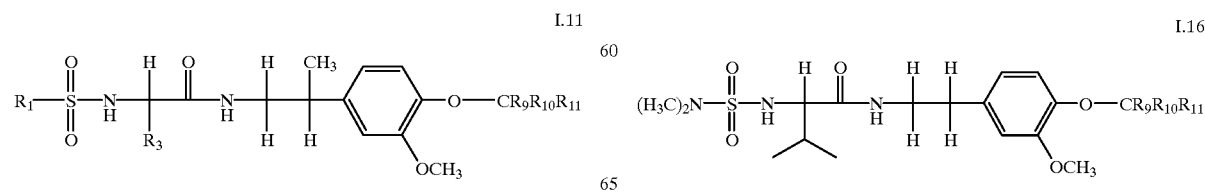

I.16

Table 17: Compounds represented by the Formula I.17 wherein the combination of the groups $R_9$, $R_{10}$ and $R_{11}$ corresponds to each row in table B.

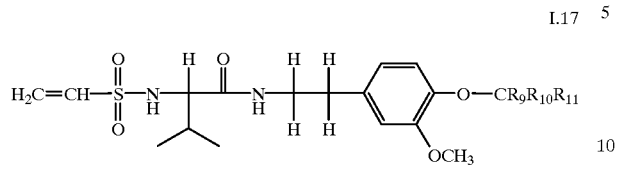

I.17

Table 18: Compounds represented by the Formula I.18 wherein the combination of the groups $R_9$, $R_{10}$ and $R_{11}$ corresponds to each row in table B.

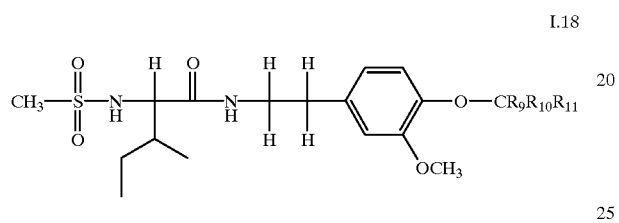

I.18

Table 19: Compounds represented by the Formula I.19 wherein the combination of the groups $R_9$, $R_{10}$ and $R_{11}$ corresponds to each row in table B.

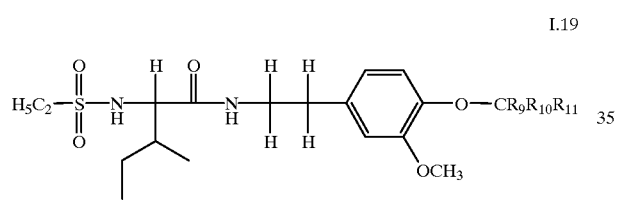

I.19

Table 20: Compounds represented by the Formula I.20 wherein the combination of the groups $R_9$, $R_{10}$ and $R_{11}$ corresponds to each row in table B.

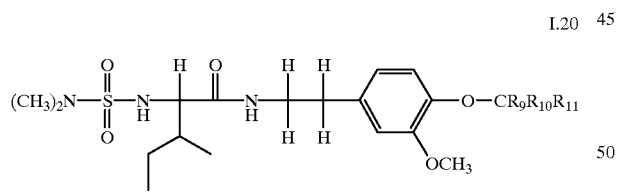

I.20

Table 21: Compounds represented by the Formula I.21 wherein the combination of the groups $R_9$, $R_{10}$ and $R_{11}$ corresponds to each row in table B.

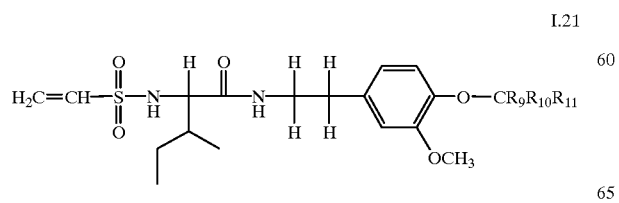

I.21

Table 22: Compounds represented by the Formula I.22 wherein the combination of the groups $R_9$, $R_{10}$ and $R_{11}$ corresponds to each row in table B.

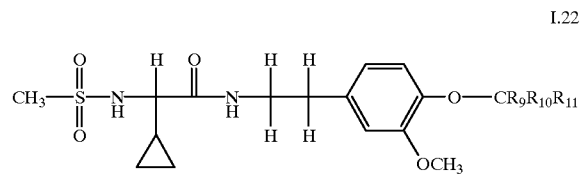

I.22

Table 23: Compounds represented by the Formula I.23 wherein the combination of the groups $R_9$, $R_{10}$ and $R_{11}$ corresponds to each row in table B.

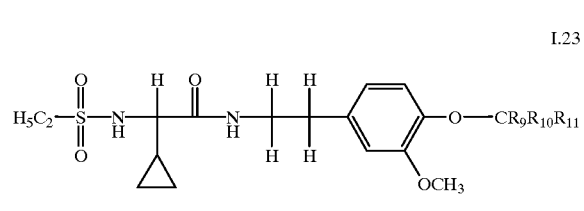

I.23

Table 24: Compounds represented by the Formula I.24 wherein the combination of the groups $R_9$, $R_{10}$ and $R_{11}$ corresponds to each row in table B.

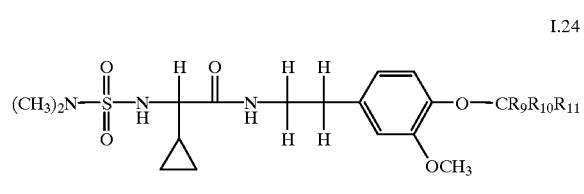

I.24

Table 25: Compounds represented by the Formula I.25 wherein the combination of the groups $R_9$, $R_{10}$ and $R_{11}$ corresponds to each row in table B.

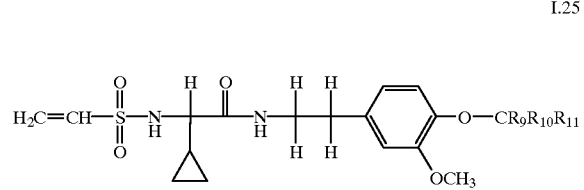

I.25

Table 26: Compounds represented by the Formula I.26 wherein the combination of the groups $R_9$, $R_{10}$ and $R_{11}$ corresponds to each row in table B.

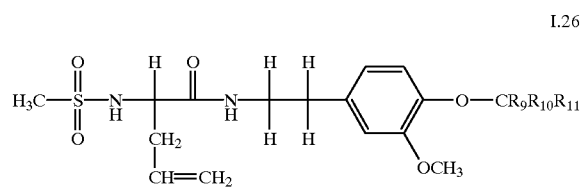

I.26

Table 27: Compounds represented by the Formula I.27 wherein the combination of the groups $R_9$, $R_{10}$ and $R_{11}$ corresponds to each row in table B.

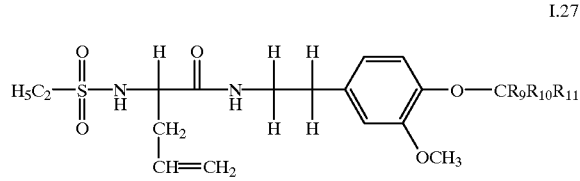

I.27

Table 28: Compounds represented by the Formula I.28 wherein the combination of the groups $R_9$, $R_{10}$ and $R_{11}$ corresponds to each row in table B.

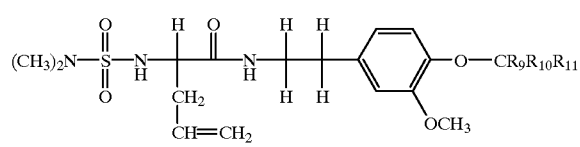

I.28

Table 29: Compounds represented by the Formula I.29 wherein the combination of the groups $R_9$, $R_{10}$ and $R_{11}$ corresponds to each row in table B.

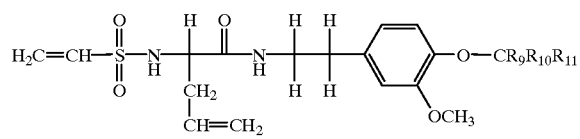

I.29

Table 30: Compounds represented by the Formula I.30 wherein the combination of the groups $R_9$, $R_{10}$ and $R_{11}$ corresponds to each row in table B.

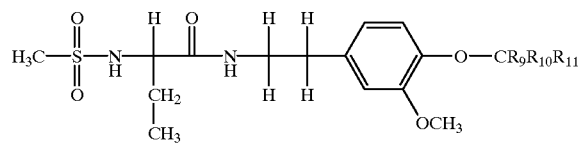

I.30

Table 31: Compounds represented by the Formula I.31 wherein the combination of the groups $R_9$, $R_{10}$ and $R_{11}$ corresponds to each row in table B.

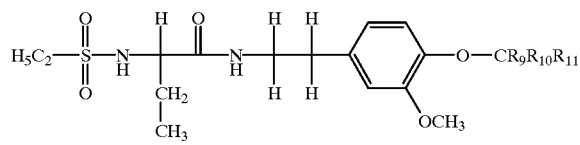

I.31

Table 32: Compounds represented by the Formula I.32 wherein the combination of the groups $R_9$, $R_{10}$ and $R_{11}$ corresponds to each row in table B.

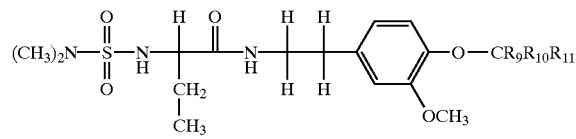

I.32

Table 33: Compounds represented by the Formula I.33 wherein the combination of the groups $R_9$, $R_{10}$ and $R_{11}$ corresponds to each row in table B.

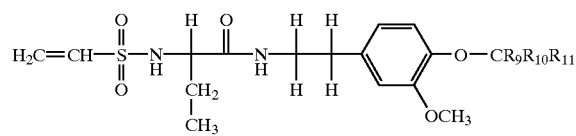

I.33

Table 34: Compounds represented by the Formula I.34 wherein the combination of the groups $R_9$, $R_{10}$ and $R_{11}$ corresponds to each row in table B.

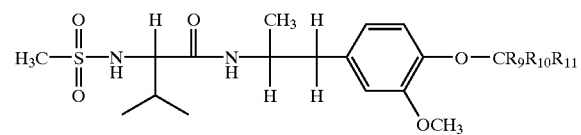

I.34

Table 35: Compounds represented by the Formula I.35 wherein the combination of the groups $R_9$, $R_{10}$ and $R_{11}$ corresponds to each row in table B.

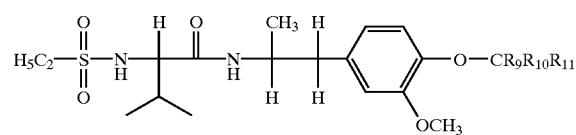

I.35

Table 36: Compounds represented by the Formula I.36 wherein the combination of the groups $R_9$, $R_{10}$ and $R_{11}$ corresponds to each row in table B.

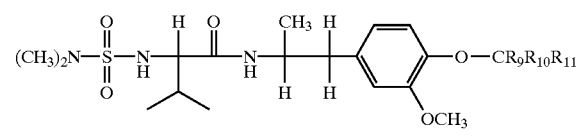

I.36

Table 37: Compounds represented by the Formula I.37 wherein the combination of the groups $R_9$, $R_{10}$ and $R_{11}$ corresponds to each row in table B.

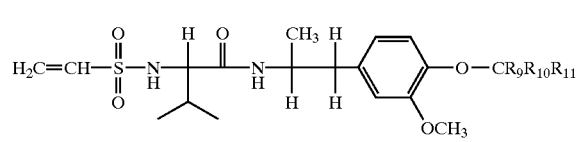

I.37

TABLE A

| No. | R₁ | R₃ | CR₉R₁₀R₁₁ |
|---|---|---|---|
| 001 | CH₃ | C₃H₇-i | CH₂—CH₂—O—(4-F—Ph) |
| 002 | C₂H₅ | C₃H₇-i | CH₂—CH₂—O—(4-F—Ph) |
| 003 | (CH₃)₂N— | C₃H₇-i | CH₂—CH₂—O—(4-F—Ph) |
| 004 | C₃H₇-i | C₃H₇-i | CH₂—CH₂—O—(4-F—Ph) |
| 005 | C₃H₇-n | C₃H₇-i | CH₂—CH₂—O—(4-F—Ph) |
| 006 | ClH₂C—CH₂—CH₂— | C₃H₇-i | CH₂—CH₂—O—(4-F—Ph) |
| 007 | H₂C=CH— | C₃H₇-i | CH₂—CH₂—O—(4-F—Ph) |
| 008 | CH₃—SO₂—CH₂— | C₃H₇-i | CH₂—CH₂—O—(4-F—Ph) |
| 009 | CF₃ | C₃H₇-i | CH₂—CH₂—O—(4-F—Ph) |
| 010 | 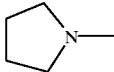 | C₃H₇-i | CH₂—CH₂—O—(4-F—Ph) |
| 011 | CH₃ | C₂H₅ | CH₂—CH₂—O—(4-F—Ph) |
| 012 | C₂H₅ | C₂H₅ | CH₂—CH₂—O—(4-F—Ph) |
| 013 | (CH₃)₂N— | C₂H₅ | CH₂—CH₂—O—(4-F—Ph) |
| 014 | C₃H₇-i | C₂H₅ | CH₂—CH₂—O—(4-F—Ph) |
| 015 | C₃H₇-n | C₂H₅ | CH₂—CH₂—O—(4-F—Ph) |
| 016 | ClH₂C—CH₂—CH₂— | C₂H₅ | CH₂—CH₂—O—(4-F—Ph) |
| 017 | H₂C=CH— | C₂H₅ | CH₂—CH₂—O—(4-F—Ph) |
| 018 | CH₃—SO₂—CH₂— | C₂H₅ | CH₂—CH₂—O—(4-F—Ph) |
| 019 | CF₃ | C₂H₅ | CH₂—CH₂—O—(4-F—Ph) |
| 020 | 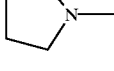 | C₂H₅ | CH₂—CH₂—O—(4-F—Ph) |
| 021 | CH₃ | C₃H₇-n | CH₂—CH₂—O—(4-F—Ph) |
| 022 | C₂H₅ | C₃H₇-n | CH₂—CH₂—O—(4-F—Ph) |
| 023 | (CH₃)₂N— | C₃H₇-n | CH₂—CH₂—O—(4-F—Ph) |
| 024 | C₃H₇-i | C₃H₇-n | CH₂—CH₂—O—(4-F—Ph) |
| 025 | C₃H₇-n | C₃H₇-n | CH₂—CH₂—O—(4-F—Ph) |
| 026 | ClH₂C—CH₂—CH₂— | C₃H₇-n | CH₂—CH₂—O—(4-F—Ph) |
| 027 | H₂C=CH— | C₃H₇-n | CH₂—CH₂—O—(4-F—Ph) |
| 028 | CH₃—SO₂—CH₂— | C₃H₇-n | CH₂—CH₂—O—(4-F—Ph) |
| 029 | CF₃ | C₃H₇-n | CH₂—CH₂—O—(4-F—Ph) |
| 030 | 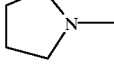 | C₃H₇-s | CH₂—CH₂—O—(4-F—Ph) |
| 031 | CH₃ | C₃H₉-s | CH₂—CH₂—O—(4-F—Ph) |
| 032 | C₂H₅ | C₃H₉-s | CH₂—CH₂—O—(4-F—Ph) |
| 033 | (CH₃)₂N— | C₃H₉-s | CH₂—CH₂—O—(4-F—Ph) |
| 034 | C₃H₇-i | C₃H₉-s | CH₂—CH₂—O—(4-F—Ph) |
| 035 | C₃H₇-n | C₃H₉-s | CH₂—CH₂—O—(4-F—Ph) |
| 036 | ClH₂C—CH₂—CH₂— | C₃H₉-s | CH₂—CH₂—O—(4-F—Ph) |
| 037 | H₂C=CH— | C₃H₉-s | CH₂—CH₂—O—(4-F—Ph) |
| 038 | CH₃—SO₂—CH₂— | C₃H₉-s | CH₂—CH₂—O—(4-F—Ph) |
| 039 | CF₃ | C₃H₉-s | CH₂—CH₂—O—(4-F—Ph) |
| 040 | 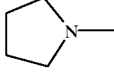 | C₃H₉-s | CH₂—CH₂—O—(4-F—Ph) |
| 041 | CH₃ | C₃H₅-cycl | CH₂—CH₂—O—(4-F—Ph) |
| 042 | C₂H₅ | C₃H₅-cycl | CH₂—CH₂—O—(4-F—Ph) |
| 043 | (CH₃)₂N— | C₃H₅-cycl | CH₂—CH₂—O—(4-F—Ph) |
| 044 | C₃H₇-i | C₃H₅-cycl | CH₂—CH₂—O—(4-F—Ph) |
| 045 | C₃H₇-n | C₃H₅-cycl | CH₂—CH₂—O—(4-F—Ph) |
| 046 | ClH₂C—CH₂—CH₂— | C₃H₅-cycl | CH₂—CH₂—O—(4-F—Ph) |
| 047 | H₂C=CH— | C₃H₅-cycl | CH₂—CH₂—O—(4-F—Ph) |
| 048 | CH₃—SO₂—CH₂— | C₃H₅-cycl | CH₂—CH₂—O—(4-F—Ph) |
| 049 | CF₃ | C₃H₅-cycl | CH₂—CH₂—O—(4-F—Ph) |
| 050 | 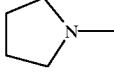 | C₃H₅-cycl | CH₂—CH₂—O—(4-F—Ph) |

TABLE A-continued

| No. | R$_1$ | R$_3$ | CR$_9$R$_{10}$R$_{11}$ |
|---|---|---|---|
| 051 | CH$_3$ | CH$_2$—CH=CH$_2$ | CH$_2$—CH$_2$—O—(4-F—Ph) |
| 052 | C$_2$H$_5$ | CH$_2$—CH=CH$_2$ | CH$_2$—CH$_2$—O—(4-F—Ph) |
| 053 | (CH$_3$)$_2$N— | CH$_2$—CH=CH$_2$ | CH$_2$—CH$_2$—O—(4-F—Ph) |
| 054 | C$_3$H$_7$-i | CH$_2$—CH=CH$_2$ | CH$_2$—CH$_2$—O—(4-F—Ph) |
| 055 | C$_3$H$_7$-n | CH$_2$—CH=CH$_2$ | CH$_2$—CH$_2$—O—(4-F—Ph) |
| 056 | ClH$_2$C—CH$_2$—CH$_2$— | CH$_2$—CH=CH$_2$ | CH$_2$—CH$_2$—O—(4-F—Ph) |
| 057 | H$_2$C=CH— | CH$_2$—CH=CH$_2$ | CH$_2$—CH$_2$—O—(4-F—Ph) |
| 058 | CH$_3$—SO$_2$—CH$_2$— | CH$_2$—CH=CH$_2$ | CH$_2$—CH$_2$—O—(4-F—Ph) |
| 059 | CF$_3$ | CH$_2$—CH=CH$_2$ | CH$_2$—CH$_2$—O—(4-F—Ph) |
| 060 | pyrrolidin-1-yl | CH$_2$—CH=CH$_2$ | CH$_2$—CH$_2$—O—(4-F—Ph) |
| 061 | CH$_3$ | CH$_2$—C≡CH | CH$_2$—CH$_2$—O—(4-F—Ph) |
| 062 | C$_2$H$_5$ | CH$_2$—C≡CH | CH$_2$—CH$_2$—O—(4-F—Ph) |
| 063 | (CH$_3$)$_2$N— | CH$_2$—C≡CH | CH$_2$—CH$_2$—O—(4-F—Ph) |
| 064 | C$_3$H$_7$-i | CH$_2$—C≡CH | CH$_2$—CH$_2$—O—(4-F—Ph) |
| 65 | C$_3$H$_7$-n | CH$_2$—C≡CH | CH$_2$—CH$_2$—O—(4-F—Ph) |
| 066 | ClH$_2$C—CH$_2$—CH$_2$— | CH$_2$—C≡CH | CH$_2$—CH$_2$—O—(4-F—Ph) |
| 067 | H$_2$C=CH— | CH$_2$—C≡CH | CH$_2$—CH$_2$—O—(4-F—Ph) |
| 068 | CH$_3$—SO$_2$—CH$_2$— | CH$_2$—C≡CH | CH$_2$—CH$_2$—O—(4-F—Ph) |
| 069 | CF$_3$ | CH$_2$—C≡CH | CH$_2$—CH$_2$—O—(4-F—Ph) |
| 070 | pyrrolidin-1-yl | CH$_2$—C≡CH | CH$_2$—CH$_2$—O—(4-F—Ph) |
| 071 | CH$_3$ | C$_3$H$_5$-cycl—CH$_2$— | CH$_2$—CH$_2$—O—(4-F—Ph) |
| 072 | C$_2$H$_5$ | C$_3$H$_5$-cycl—CH$_2$— | CH$_2$—CH$_2$—O—(4-F—Ph) |
| 073 | (CH$_3$)$_2$N— | C$_3$H$_5$-cycl—CH$_2$— | CH$_2$—CH$_2$—O—(4-F—Ph) |
| 074 | C$_3$H$_7$-i | C$_3$H$_5$-cycl—CH$_2$— | CH$_2$—CH$_2$—O—(4-F—Ph) |
| 075 | C$_3$H$_7$-n | C$_3$H$_5$-cycl—CH$_2$— | CH$_2$—CH$_2$—O—(4-F—Ph) |
| 076 | ClH$_2$C—CH$_2$—CH$_2$— | C$_3$H$_5$-cycl—CH$_2$— | CH$_2$—CH$_2$—O—(4-F—Ph) |
| 077 | H$_2$C=CH— | C$_3$H$_5$-cycl—CH$_2$— | CH$_2$—CH$_2$—O—(4-F—Ph) |
| 078 | CH$_3$—SO$_2$—CH$_2$— | C$_3$H$_5$-cycl—CH$_2$— | CH$_2$—CH$_2$—O—(4-F—Ph) |
| 079 | CF$_3$ | C$_3$H$_5$-cycl—CH$_2$— | CH$_2$—CH$_2$—O—(4-F—Ph) |
| 080 | pyrrolidin-1-yl | C$_3$H$_5$-cycl—CH$_2$— | CH$_2$—CH$_2$—O—(4-F—Ph) |
| 081 | CH$_3$ | H$_3$C—CH$_2$(OH)— | CH$_2$—CH$_2$—O—(4-F—Ph) |
| 082 | C$_2$H$_5$ | H$_3$C—CH$_2$(OH)— | CH$_2$—CH$_2$—O—(4-F—Ph) |
| 083 | (CH$_3$)$_2$N— | H$_3$C—CH$_2$(OH)— | CH$_2$—CH$_2$—O—(4-F—Ph) |
| 084 | C$_3$H$_7$-i | H$_3$C—CH$_2$(OH)— | CH$_2$—CH$_2$—O—(4-F—Ph) |
| 085 | C$_3$H$_7$-n | H$_3$C—CH$_2$(OH)— | CH$_2$—CH$_2$—O—(4-F—Ph) |
| 086 | ClH$_2$C—CH$_2$—CH$_2$— | H$_3$C—CH$_2$(OH)— | CH$_2$—CH$_2$—O—(4-F—Ph) |
| 087 | H$_2$C=CH— | H$_3$C—CH$_2$(OH)— | CH$_2$—CH$_2$—O—(4-F—Ph) |
| 088 | CH$_3$—SO$_2$—CH$_2$— | H$_3$C—CH$_2$(OH)— | CH$_2$—CH$_2$—O—(4-F—Ph) |
| 089 | CF$_3$ | H$_3$C—CH$_2$(OH)— | CH$_2$—CH$_2$—O—(4-F—Ph) |
| 090 | pyrrolidin-1-yl | H$_3$C—CH$_2$(OH)— | CH$_2$—CH$_2$—O—(4-F—Ph) |
| 091 | CH$_3$ | H$_3$C—S—CH$_2$—CH$_2$— | CH$_2$—CH$_2$—O—(4-F—Ph) |
| 092 | C$_2$H$_5$ | H$_3$C—S—CH$_2$—CH$_2$— | CH$_2$—CH$_2$—O—(4-F—Ph) |
| 093 | (CH$_3$)$_2$N— | H$_3$C—S—CH$_2$—CH$_2$— | CH$_2$—CH$_2$—O—(4-F—Ph) |
| 094 | C$_3$H$_7$-i | H$_3$C—S—CH$_2$—CH$_2$— | CH$_2$—CH$_2$—O—(4-F—Ph) |
| 095 | C$_3$H$_7$-n | H$_3$C—S—CH$_2$—CH$_2$— | CH$_2$—CH$_2$—O—(4-F—Ph) |
| 096 | ClH$_2$C—CH$_2$—CH$_2$— | H$_3$C—S—CH$_2$—CH$_2$— | CH$_2$—CH$_2$—O—(4-F—Ph) |
| 097 | H$_2$C=CH— | H$_3$C—S—CH$_2$—CH$_2$— | CH$_2$—CH$_2$—O—(4-F—Ph) |
| 098 | CH$_3$—SO$_2$CH$_2$— | H$_3$C—S—CH$_2$—CH$_2$— | CH$_2$—CH$_2$—O—(4-F—Ph) |
| 099 | CF$_3$ | H$_3$C—S—CH$_2$—CH$_2$— | CH$_2$—CH$_2$—O—(4-F—Ph) |
| 100 | pyrrolidin-1-yl | H$_3$C—S—CH$_2$—CH$_2$— | CH$_2$—CH$_2$—O—(4-F—Ph) |

TABLE A-continued

| No. | R$_1$ | R$_3$ | CR$_9$R$_{10}$R$_{11}$ |
|---|---|---|---|
| 101 | CH$_3$ | HS—CH$_2$ | CH$_2$—CH$_2$—O—(4-F—Ph) |
| 102 | C$_2$H$_5$ | HS—CH$_2$ | CH$_2$—CH$_2$—O—(4-F—Ph) |
| 103 | (CH$_3$)$_2$N— | HS—CH$_2$ | CH$_2$—CH$_2$—O—(4-F—Ph) |
| 104 | C$_3$H$_7$-i | HS—CH$_2$ | CH$_2$—CH$_2$—O—(4-F—Ph) |
| 105 | C$_3$H$_7$-n | HS—CH$_2$ | CH$_2$—CH$_2$—O—(4-F—Ph) |
| 106 | ClH$_2$C—CH$_2$—CH$_2$— | HS—CH$_2$ | CH$_2$—CH$_2$—O—(4-F—Ph) |
| 107 | H$_2$C=CH— | HS—CH$_2$ | CH$_2$—CH$_2$—O—(4-F—Ph) |
| 108 | CH$_3$—SO$_2$CH$_2$— | HS—CH$_2$ | CH$_2$—CH$_2$—O—(4-F—Ph) |
| 109 | CF$_3$ | HS—CH$_2$ | CH$_2$—CH$_2$—O—(4-F—Ph) |
| 110 | 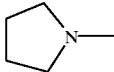 | HS—CH$_2$ | CH$_2$—CH$_2$—O—(4-F—Ph) |
| 111 | CH$_3$ | C$_3$H$_7$-i | CH$_2$—CH$_2$—O—(4-Cl—Ph) |
| 112 | C$_2$H$_5$ | C$_3$H$_7$-i | CH$_2$—CH$_2$—O—(4-Cl—Ph) |
| 113 | (CH$_3$)$_2$N— | C$_3$H$_7$-i | CH$_2$—CH$_2$—O—(4-Cl—Ph) |
| 114 | C$_3$H$_7$-i | C$_3$H$_7$-i | CH$_2$—CH$_2$—O—(4-Cl—Ph) |
| 115 | C$_3$H$_7$-n | C$_3$H$_7$-i | CH$_2$—CH$_2$—O—(4-Cl—Ph) |
| 116 | ClH$_2$C—CH$_2$—CH$_2$— | C$_3$H$_7$-i | CH$_2$—CH$_2$—O—(4-Cl—Ph) |
| 117 | H$_2$C=CH— | C$_3$H$_7$-i | CH$_2$—CH$_2$—O—(4-Cl—Ph) |
| 118 | CH$_3$—SO$_2$—CH$_2$— | C$_3$H$_7$-i | CH$_2$—CH$_2$—O—(4-Cl—Ph) |
| 119 | CF$_3$ | C$_3$H$_7$-i | CH$_2$—CH$_2$—O—(4-Cl—Ph) |
| 120 | 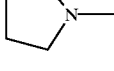 | C$_3$H$_7$-i | CH$_2$—CH$_2$—O—(4-Cl—Ph) |
| 121 | CH$_3$ | C$_2$H$_5$ | CH$_2$—CH$_2$—O—(4-Cl—Ph) |
| 122 | C$_2$H$_5$ | C$_2$H$_5$ | CH$_2$—CH$_2$—O—(4-Cl—Ph) |
| 123 | (CH$_3$)$_2$N— | C$_2$H$_5$ | CH$_2$—CH$_2$—O—(4-Cl—Ph) |
| 124 | C$_3$H$_7$-i | C$_2$H$_5$ | CH$_2$—CH$_2$—O—(4-Cl—Ph) |
| 125 | C$_3$H$_7$-n | C$_2$H$_5$ | CH$_2$—CH$_2$—O—(4-Cl—Ph) |
| 126 | ClH$_2$C—CH$_2$—CH$_2$— | C$_2$H$_5$ | CH$_2$—CH$_2$—O—(4-Cl—Ph) |
| 127 | H$_2$C=CH— | C$_2$H$_5$ | CH$_2$—CH$_2$—O—(4-Cl—Ph) |
| 128 | CH$_3$—SO$_2$—CH$_2$— | C$_2$H$_5$ | CH$_2$—CH$_2$—O—(4-Cl—Ph) |
| 129 | CF$_3$ | C$_2$H$_5$ | CH$_2$—CH$_2$—O—(4-Cl—Ph) |
| 130 | 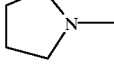 | C$_2$H$_5$ | CH$_2$—CH$_2$—O—(4-Cl—Ph) |
| 131 | CH$_3$ | C$_3$H$_7$-n | CH$_2$—CH$_2$—O—(4-Cl—Ph) |
| 132 | C$_2$H$_5$ | C$_3$H$_7$-n | CH$_2$—CH$_2$—O—(4-Cl—Ph) |
| 133 | (CH$_3$)$_2$N— | C$_3$H$_7$-n | CH$_2$—CH$_2$—O—(4-Cl—Ph) |
| 134 | C$_3$H$_7$-i | C$_3$H$_7$-n | CH$_2$—CH$_2$—O—(4-Cl—Ph) |
| 135 | C$_3$H$_7$-n | C$_3$H$_7$-n | CH$_2$—CH$_2$—O—(4-Cl—Ph) |
| 136 | ClH$_2$C—CH$_2$—CH$_2$— | C$_3$H$_7$-n | CH$_2$—CH$_2$—O—(4-Cl—Ph) |
| 137 | H$_2$C=CH— | C$_3$H$_7$-n | CH$_2$—CH$_2$—O—(4-Cl—Ph) |
| 138 | CH$_3$—SO$_2$—CH$_2$— | C$_3$H$_7$-n | CH$_2$—CH$_2$—O—(4-Cl—Ph) |
| 139 | CF$_3$ | C$_3$H$_7$-n | CH$_2$—CH$_2$—O—(4-Cl—Ph) |
| 140 | 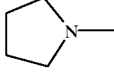 | C$_3$H$_7$-n | CH$_2$—CH$_2$—O—(4-Cl—Ph) |
| 141 | CH$_3$ | C$_4$H$_9$-s | CH$_2$—CH$_2$—O—(4-Cl—Ph) |
| 142 | C$_2$H$_5$ | C$_4$H$_9$-s | CH$_2$—CH$_2$—O—(4-Cl—Ph) |
| 143 | (CH$_3$)$_2$N— | C$_4$H$_9$-s | CH$_2$—CH$_2$—O—(4-Cl—Ph) |
| 144 | C$_3$H$_7$-i | C$_4$H$_9$-s | CH$_2$—CH$_2$—O—(4-Cl—Ph) |
| 145 | C$_3$H$_7$-n | C$_4$H$_9$-s | CH$_2$—CH$_2$—O—(4-Cl—Ph) |
| 146 | ClH$_2$C—CH$_2$—CH$_2$— | C$_4$H$_9$-s | CH$_2$—CH$_2$—O—(4-Cl—Ph) |
| 147 | H$_2$C=CH— | C$_4$H$_9$-s | CH$_2$—CH$_2$—O—(4-Cl—Ph) |
| 148 | CH$_3$—SO$_2$—CH$_2$— | C$_4$H$_9$-s | CH$_2$—CH$_2$—O—(4-Cl—Ph) |
| 149 | CF$_3$ | C$_4$H$_9$-s | CH$_2$—CH$_2$—O—(4-Cl—Ph) |
| 150 | 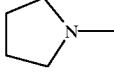 | C$_4$H$_9$-s | CH$_2$—CH$_2$—O—(4-Cl—Ph) |

TABLE A-continued

| No. | R₁ | R₃ | CR₉R₁₀R₁₁ |
|---|---|---|---|
| 151 | CH₃ | C₃H₅-cycl | CH₂—CH₂—O—(4-Cl—Ph) |
| 152 | C₂H₅ | C₃H₅-cycl | CH₂—CH₂—O—(4-Cl—Ph) |
| 153 | (CH₃)₂N— | C₃H₅-cycl | CH₂—CH₂—O—(4-Cl—Ph) |
| 154 | C₃H₇-i | C₃H₅-cycl | CH₂—CH₂—O—(4-Cl—Ph) |
| 155 | C₃H₇-n | C₃H₅-cycl | CH₂—CH₂—O—(4-Cl—Ph) |
| 156 | ClH₂C—CH₂—CH₂— | C₃H₅-cycl | CH₂—CH₂—O—(4-Cl—Ph) |
| 157 | H₂C=CH— | C₃H₅-cycl | CH₂—CH₂—O—(4-Cl—Ph) |
| 158 | CH₃—SO₂—CH₂— | C₃H₅-cycl | CH₂—CH₂—O—(4-Cl—Ph) |
| 159 | CF₃ | C₃H₅-cycl | CH₂—CH₂—O—(4-Cl—Ph) |
| 160 | pyrrolidin-1-yl | C₃H₅-cycl | CH₂—CH₂—O—(4-Cl—Ph) |
| 161 | CH₃ | CH₂—CH=CH₂ | CH₂—CH₂—O—(4-Cl—Ph) |
| 162 | C₂H₅ | CH₂—CH=CH₂ | CH₂—CH₂—O—(4-Cl—Ph) |
| 163 | (CH₃)₂N— | CH₂—CH=CH₂ | CH₂—CH₂—O—(4-Cl—Ph) |
| 164 | C₃H₇-i | CH₂—CH=CH₂ | CH₂—CH₂—O—(4-Cl—Ph) |
| 165 | C₃H₇-n | CH₂—CH=CH₂ | CH₂—CH₂—O—(4-Cl—Ph) |
| 166 | ClH₂C—CH₂—CH₂— | CH₂—CH=CH₂ | CH₂—CH₂—O—(4-Cl—Ph) |
| 167 | H₂C=CH— | CH₂—CH=CH₂ | CH₂—CH₂—O—(4-Cl—Ph) |
| 168 | CH₃—SO₂CH₂— | CH₂—CH=CH₂ | CH₂—CH₂—O—(4-Cl—Ph) |
| 169 | CF₃ | CH₂—CH=CH₂ | CH₂—CH₂—O—(4-Cl—Ph) |
| 170 | pyrrolidin-1-yl | CH₂—CH=CH₂ | CH₂—CH₂—O—(4-Cl—Ph) |
| 171 | CH₃ | CH₂—C≡CH | CH₂—CH₂—O—(4-Cl—Ph) |
| 172 | C₂H₅ | CH₂—C≡CH | CH₂—CH₂—O—(4-Cl—Ph) |
| 173 | (CH₃)₂N— | CH₂—C≡CH | CH₂—CH₂—O—(4-Cl—Ph) |
| 174 | C₃H₇-i | CH₂—C≡CH | CH₂—CH₂—O—(4-Cl—Ph) |
| 175 | C₃H₇-n | CH₂—C≡CH | CH₂—CH₂—O—(4-Cl—Ph) |
| 176 | ClH₂C—CH₂—CH₂— | CH₂—C≡CH | CH₂—CH₂—O—(4-Cl—Ph) |
| 177 | H₂C=CH— | CH₂—C≡CH | CH₂—CH₂—O—(4-Cl—Ph) |
| 178 | CH₃—SO₂—CH₂— | CH₂—C≡CH | CH₂—CH₂—O—(4-Cl—Ph) |
| 179 | CF₃ | CH₂—C≡CH | CH₂—CH₂—O—(4-Cl—Ph) |
| 180 | pyrrolidin-1-yl | CH₂—C≡CH | CH₂—CH₂—O—(4-Cl—Ph) |
| 181 | CH₃ | C₃H₅-cycl—CH₂— | CH₂—CH₂—O—(4-Cl—Ph) |
| 182 | C₂H₅ | C₃H₅-cycl—CH₂— | CH₂—CH₂—O—(4-Cl—Ph) |
| 183 | (CH₃)₂N— | C₃H₅-cycl—CH₂— | CH₂—CH₂—O—(4-Cl—Ph) |
| 184 | C₃H₇-i | C₃H₅-cycl—CH₂— | CH₂—CH₂—O—(4-Cl—Ph) |
| 185 | C₃H₇-n | C₃H₅-cycl—CH₂— | CH₂—CH₂—O—(4-Cl—Ph) |
| 186 | ClH₂C—CH₂—CH₂— | C₃H₅-cycl—CH₂— | CH₂—CH₂—O—(4-Cl—Ph) |
| 187 | H₂C=CH— | C₃H₅-cycl—CH₂— | CH₂—CH₂—O—(4-Cl—Ph) |
| 188 | CH₃—SO₂—CH₂— | C₃H₅-cycl—CH₂— | CH₂—CH₂—O—(4-Cl—Ph) |
| 189 | CF₃ | C₃H₅-cycl—CH₂— | CH₂—CH₂—O—(4-Cl—Ph) |
| 190 | pyrrolidin-1-yl | C₃H₅-cycl—CH₂— | CH₂—CH₂—O—(4-Cl—Ph) |
| 191 | CH₃ | H₃C—CH₂(OH)— | CH₂—CH₂—O—(4-Cl—Ph) |
| 192 | C₂H₅ | H₃C—CH₂(OH)— | CH₂—CH₂—O—(4-Cl—Ph) |
| 193 | (CH₃)₂N— | H₃C—CH₂(OH)— | CH₂—CH₂—O—(4-Cl—Ph) |
| 194 | C₃H₇-i | H₃C—CH₂(OH)— | CH₂—CH₂—O—(4-Cl—Ph) |
| 195 | C₃H₇-n | H₃C—CH₂(OH)— | CH₂—CH₂—O—(4-Cl—Ph) |
| 196 | ClH₂C—CH₂—CH₂— | H₃C—CH₂(OH)— | CH₂—CH₂—O—(4-Cl—Ph) |
| 197 | H₂C=CH— | H₃C—CH₂(OH)— | CH₂—CH₂—O—(4-Cl—Ph) |
| 198 | CH₃—SO₂—CH₂— | H₃C—CH₂(OH)— | CH₂—CH₂—O—(4-Cl—Ph) |
| 199 | CF₃ | H₃C—CH₂(OH)— | CH₂—CH₂—O—(4-Cl—Ph) |
| 200 | pyrrolidin-1-yl | H₃C—CH₂(OH)— | CH₂—CH₂—O—(4-Cl—Ph) |

TABLE A-continued

| No. | R₁ | R₃ | CR₉R₁₀R₁₁ |
|-----|----|----|-----------|
| 201 | CH₃ | H₃C—S—CH₂—CH₂—CH₂—CH₂—O—(4-Cl—Ph) | |
| 202 | C₂H₅ | H₃C—S—CH₂—CH₂—CH₂—CH₂—O—(4-Cl—Ph) | |
| 203 | (CH₃)₂N— | H₃C—S—CH₂—CH₂—CH₂—CH₂—O—(4-Cl—Ph) | |
| 204 | C₃H₇-i | H₃C—S—CH₂—CH₂—CH₂—CH₂—O—(4-Cl—Ph) | |
| 205 | C₃H₇-n | H₃C—S—CH₂—CH₂—CH₂—CH₂—O—(4-Cl—Ph) | |
| 206 | ClH₂C—CH₂—CH₂— | H₃C—S—CH₂—CH₂—CH₂—CH₂—O—(4-Cl—Ph) | |
| 207 | H₂C=CH— | H₃C—S—CH₂—CH₂—CH₂—CH₂—O—(4-Cl—Ph) | |
| 208 | CH₃—SO₂—CH₂— | H₃C—S—CH₂—CH₂—CH₂—CH₂—O—(4-Cl—Ph) | |
| 209 | CF₃ | H₃C—S—CH₂—CH₂—CH₂—CH₂—O—(4-Cl—Ph) | |
| 210 | pyrrolidin-1-yl | H₃C—S—CH₂—CH₂—CH₂—CH₂—O—(4-Cl—Ph) | |
| 211 | CH₃ | HS—CH₂ | CH₂—CH₂—O—(4-Cl—Ph) |
| 212 | C₂H₅ | HS—CH₂ | CH₂—CH₂—O—(4-Cl—Ph) |
| 213 | (CH₃)₂N— | HS—CH₂ | CH₂—CH₂—O—(4-Cl—Ph) |
| 214 | C₃H₇-i | HS—CH₂ | CH₂—CH₂—O—(4-Cl—Ph) |
| 215 | C₃H₇-n | HS—CH₂ | CH₂—CH₂—O—(4-Cl—Ph) |
| 216 | ClH₂C—CH₂—CH₂— | HS—CH₂ | CH₂—CH₂—O—(4-Cl—Ph) |
| 217 | H₂C=CH— | HS—CH₂ | CH₂—CH₂—O—(4-Cl—Ph) |
| 218 | CH₃—SO₂—CH₂— | HS—CH₂ | CH₂—CH₂—O—(4-Cl—Ph) |
| 219 | CF₃ | HS—CH₂ | CH₂—CH₂—O—(4-Cl—Ph) |
| 220 | pyrrolidin-1-yl | HS—CH₂ | CH₂—CH₂—O—(4-Cl—Ph) |

TABLE B

| No. | CR₉R₁₀R₁₁ |
|-----|-----------|
| 001 | CH₂—CH=CH—Ph |
| 002 | CH₂—CH=CH—(4-F—Ph) |
| 003 | CH₂—CH=CH—(4-Cl—Ph) |
| 004 | CH₂—CH=CH—(4-Br—Ph) |
| 005 | CH₂—CH=CH—(4-CH₃—Ph) |
| 006 | CH₂—CH=CH—(4-OCH₃—Ph) |
| 007 | CH₂—CH=CH—(4-NO₂—Ph) |
| 008 | CH₂—CH=CH—(4-CF₃—Ph) |
| 009 | CH₂—CH=CH—(4-CN—Ph) |
| 010 | CH₂—CH=CH—(3-Br—Ph) |
| 011 | CH₂—CH=CH—(3-Cl—Ph) |
| 012 | CH₂—CH=CH—(3-Cl—Ph) |
| 013 | CH₂—CH=CH—(3-CH₃—Ph) |
| 014 | CH₂—CH=CH—(2-Cl—Ph) |
| 015 | CH₂—CH=CH—(2-F—Ph) |
| 016 | CH₂—CH=CH—(2,4-Cl₂—Ph) |
| 017 | CH₂—CH=CH—(3-Cl—4-CH₃—Ph) |
| 018 | CH₂—CH=CH—(3-Cl—4-F—Ph) |
| 019 | CH₂—CH=CH—(3-F—4-Cl—Ph) |
| 020 | CH₂—CH=CH—(3,4-Cl₂—Ph) |
| 021 | CH₂—CH=CH—(3,4-F₂—Ph) |
| 022 | CH₂—CH=CH—(2,5-Cl₂—Ph) |
| 023 | CH₂—CH=CH—(3,5-Cl₂—Ph) |
| 024 | CH₂—CH=CH—2,4,5-Cl₃—Ph) |
| 025 | —CH₂—CH=CH—(1-naphthyl) |
| 026 | —CH₂—CH=CH—(2-naphthyl) |
| 027 | —CH₂—CH=CH—(2-thienyl) |
| 028 | —CH₂—CH=CH—(2-furyl) |
| 029 | —CH₂—CH=CH—(2-pyrrolyl) |
| 030 | —CH₂—CH=CH—(3-indolyl) |
| 031 | —CH₂—CH=CH—(2-benzothienyl) |

TABLE B-continued

| No. | CR$_9$R$_{10}$R$_{11}$ |
|---|---|
| 032 | 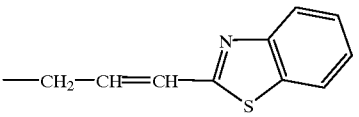 —CH$_2$—CH=CH—(benzothiazol-2-yl) |
| 033 | 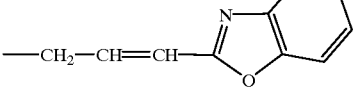 —CH$_2$—CH=CH—(benzoxazol-2-yl) |
| 034 | CH(CH$_3$)—CH=CH—Ph |
| 035 | CH(CH$_3$)—CH=CH—(4-F—Ph) |
| 036 | CH(CH$_3$)—CH=CH—(4-Cl—Ph) |
| 037 | CH(CH$_3$)—CH=CH—(4-Br—Ph) |
| 038 | C(CH$_3$)$_2$—CH=CH—Ph |
| 039 | C(CH$_3$)$_2$—CH=CH—(4-F—Ph) |
| 040 | C(CH$_3$)$_2$—CH=CH—(4-Cl—Ph) |
| 041 | CH$_2$—C(CH$_3$)=CH—Ph |
| 042 | CH$_2$—C(CH$_3$)=CH—(4-F—Ph) |
| 043 | CH$_2$—C(CH$_3$)=CH—(4-F—Ph) |
| 044 | CH$_2$—C(CH$_3$)=C(CH$_3$)—Ph |
| 045 | CH$_2$—C(CH$_3$)=C(CH$_3$)—(4-F—Ph) |
| 046 | CH$_2$—C(CH$_3$)=C(CH$_3$)—(4-Cl—Ph) |
| 047 | CH$_2$—CH=C(CH$_3$)—Ph |
| 048 | CH$_2$—CH=C(CH$_3$)—(4-F—Ph) |
| 049 | CH$_2$—CH=C(CH$_3$)—(4-Cl—Ph) |
| 050 | CH$_2$—CH$_2$—O—Ph |
| 051 | CH$_2$—CH$_2$—O—(4-Br—Ph) |
| 052 | CH$_2$—CH$_2$—O—(4-I—Ph) |
| 053 | CH$_2$—CH$_2$—O—(4-CH$_3$—Ph) |
| 054 | CH$_2$—CH$_2$—O—[4-(C$_3$H$_7$-i)—Ph] |
| 055 | CH$_2$—CH$_2$—O—(4-CF$_3$—Ph) |
| 056 | CH$_2$—CH$_2$—O—(4-OCH$_3$—Ph) |
| 057 | CH$_2$—CH$_2$—O—(4-OCF$_3$—Ph) |
| 058 | CH$_2$—CH$_2$—O—(4-SCF$_3$—Ph) |
| 059 | CH$_2$—CH$_2$—O—(4-SCH$_3$—Ph) |
| 060 | CH$_2$—CH$_2$—O—(4-CN—Ph) |
| 061 | CH$_2$—CH$_2$—O—(4-NO$_2$—Ph) |
| 062 | CH$_2$—CH$_2$—O—(4-CH$_3$OOC—Ph) |
| 063 | CH$_2$—CH$_2$—O—[4-(CH$_2$=CH)—Ph] |
| 064 | CH$_2$—CH$_2$—O—[4-(CH≡C)—Ph] |
| 065 | CH$_2$—CH$_2$—O—[4-(CH$_2$—Ph)—Ph] |
| 066 | CH$_2$—CH$_2$—O—[4-(C$_6$H$_{11}$-cycl)—Ph] |
| 067 | CH$_2$—CH$_2$—O—[4-(CH$_3$—SO$_2$)—Ph] |
| 068 | CH$_2$—CH$_2$—O—(4-CHO—Ph) |
| 069 | CH$_2$—CH$_2$—O—[4-(CH$_3$—CO)—Ph] |
| 070 | CH$_2$—CH$_2$—O—(4-OH—Ph) |
| 071 | CH$_2$—CH$_2$—O—(4-NH$_2$—Ph) |
| 072 | CH$_2$—CH$_2$—O—[4-(CH$_3$)$_2$N—Ph] |
| 073 | CH$_2$—CH$_2$—O—[4-(CH$_2$=CH—CH$_2$)OOC—Ph] |
| 074 | CH$_2$—CH$_2$—O—(3-F—Ph) |
| 075 | CH$_2$—CH$_2$—O—(3-Cl—Ph) |
| 076 | CH$_2$—CH$_2$—O—(3-Br—Ph) |
| 077 | CH$_2$—CH$_2$—O—(3-OCHF$_2$—Ph) |
| 078 | CH$_2$—CH$_2$—O—(3-CH$_3$—Ph) |
| 079 | CH$_2$—CH$_2$—O—(3-CF$_3$—Ph) |
| 080 | CH$_2$—CH$_2$—O—(2-F—Ph) |
| 081 | CH$_2$—CH$_2$—O—(2-Cl—Ph) |
| 082 | CH$_2$—CH$_2$—O—(3,4-Cl$_2$—Ph) |
| 083 | CH$_2$—CH$_2$—O—[3,4-(CH$_3$)$_2$—Ph] |
| 084 | CH$_2$—CH$_2$—O—(3,4-F$_2$—Ph) |
| 085 | CH$_2$—CH$_2$—O—(3-Cl—4-F—Ph) |
| 086 | CH$_2$—CH$_2$—O—(3-F—4-Cl—Ph) |
| 087 | CH$_2$—CH$_2$—O—(3-CH$_3$—4-Cl—Ph) |
| 088 | CH$_2$—CH$_2$—O—(2,5-Cl$_2$—Ph) |
| 089 | CH$_2$—CH$_2$—O—(2,6-Cl$_2$—Ph) |
| 090 | CH$_2$—CH$_2$—O—(2,4-Cl$_2$—Ph) |
| 091 | CH$_2$—CH$_2$—O—(2,4-F$_2$—Ph) |
| 092 | CH$_2$—CH$_2$—O—(3,5-F$_2$—Ph) |
| 093 | CH$_2$—CH$_2$—O—(3,5-Cl$_2$—Ph) |
| 094 | CH$_2$—CH$_2$—O—(2,4,5-Cl$_3$—Ph) |
| 095 | CH$_2$—CH$_2$—O—(2,3,4,5,6-F$_5$—Ph) |
| 096 | 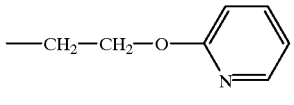 —CH$_2$—CH$_2$—O—(pyridin-2-yl) |
| 097 | 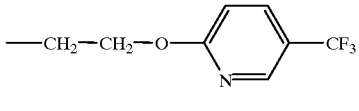 —CH$_2$—CH$_2$—O—(5-CF$_3$-pyridin-2-yl) |
| 098 | 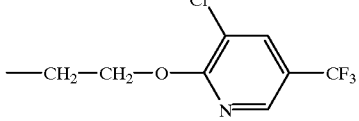 —CH$_2$—CH$_2$—O—(3-Cl-5-CF$_3$-pyridin-2-yl) |
| 099 | 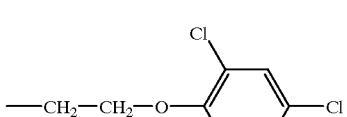 —CH$_2$—CH$_2$—O—(3,5-Cl$_2$-pyridin-2-yl) |
| 100 |  —CH$_2$—CH$_2$—O—(3,5-Cl$_2$-pyridin-4-yl) |
| 101 | 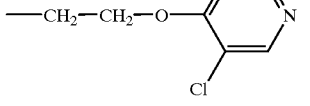 —CH$_2$—CH$_2$—O—(pyridin-4-yl) |
| 102 | 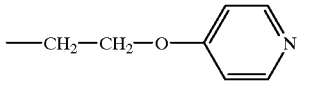 —CH$_2$—CH$_2$—O—(pyrimidin-2-yl) |
| 103 | 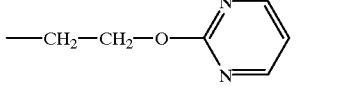 —CH$_2$—CH$_2$—O—(4,6-(OCH$_3$)$_2$-pyrimidin-2-yl) |
| 104 | 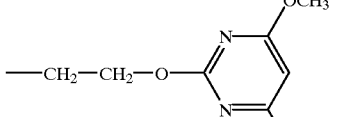 —CH$_2$—CH$_2$—O—(1,3,5-triazin-2-yl) |
| 105 |  —CH$_2$—CH=CH—(quinolin-2-yl) |
| 106 | CH(CH$_3$)—CH$_2$—O—Ph |
| 107 | CH(CH$_3$)—CH$_2$—O—(4-F—Ph) |
| 108 | CH(CH$_3$)—CH$_2$—O—(4-Cl—Ph) |
| 109 | CH(C$_2$H$_5$)—CH$_2$—O—(4-F—Ph) |
| 110 | CH(C$_2$H$_5$)—CH$_2$—O—(4-Cl—Ph) |
| 111 | C(CH$_3$)$_2$—CH$_2$—O—(4-F—Ph) |
| 112 | C(CH$_3$)$_2$—CH$_2$—O—(4-Cl—Ph) |

TABLE B-continued

| No. | CR$_9$R$_{10}$R$_{11}$ |
|---|---|
| 113 | CH$_2$—CH(CH$_3$)—O—Ph |
| 114 | CH$_2$—CH(CH$_3$)—O—(4-F—Ph) |
| 115 | CH$_2$—CH(CH$_3$)—O—(4-Cl—Ph) |
| 116 | CH$_2$—CH$_2$—S—Ph |
| 117 | CH$_2$—CH$_2$—S—(4-F—Ph) |
| 118 | CH$_2$—CH$_2$—S—(4-Cl—Ph) |
| 119 | CH$_2$—CH$_2$—S—(4-Br—Ph) |
| 120 | CH$_2$—CH$_2$—S—(3-F—Ph) |
| 121 | CH$_2$—CH$_2$—S—(3-Cl—Ph) |
| 122 | CH$_2$—CH$_2$—S—(3-Br—Ph) |
| 123 | CH$_2$—CH$_2$—S—(3,4-F$_2$—Ph) |
| 124 | CH$_2$—CH$_2$—S—(3,4-Cl$_2$—Ph) |
| 125 | CH$_2$—CH$_2$—NH—Ph |
| 126 | CH$_2$—CH$_2$—NH—(4-F—Ph) |
| 127 | CH$_2$—CH$_2$—NH—(4-Cl—Ph) |
| 128 | CH$_2$—CH$_2$—NH—(4-Br—Ph) |
| 129 | CH$_2$—CH$_2$—NH—(3-F—Ph) |
| 130 | CH$_2$—CH$_2$—NH—(3-Cl—Ph) |
| 131 | CH$_2$—CH$_2$—NH—(3-Br—Ph) |
| 132 | CH$_2$—CH$_2$—NH—(3,4-F$_2$—Ph) |
| 133 | CH$_2$—CH$_2$—NH—(3,4-Cl$_2$—Ph) |
| 134 | CH$_2$—CH$_2$—N(CH$_3$)—Ph |
| 135 | CH$_2$—CH$_2$—N(CH$_3$)—(4-F—Ph) |
| 136 | CH$_2$—CH$_2$—N(CH$_3$)—(4-Cl—Ph) |
| 137 | CH$_2$—CH$_2$—N(CH$_3$)—(4-Br—Ph) |
| 138 | CH$_2$—CH$_2$—N(CH$_3$)—(3-F—Ph) |
| 139 | CH$_2$—CH$_2$—N(CH$_3$)—(3-Cl—Ph) |
| 140 | CH$_2$—CH$_2$—N(CH$_3$)—(3-Br—Ph) |
| 141 | CH$_2$—CH$_2$—N(CH$_3$)—(3,4-F$_2$—Ph) |
| 142 | CH$_2$—CH$_2$—N(CH$_3$)—(3,4-Cl$_2$—Ph) |

Formulations may be prepared analogously to those described in, for example, WO 95/30651.

Biological Examples

D-1: Action against Plasmopara Viticola on Vines a) Residual-protective Action

Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-curative Action

Vine seedlings are infected at the 4- to 5-leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 to 37 exhibit a good fungicidal action against Plasmopara viticola on vines. Compounds A1.02, A1.03, A1.04, A1.03, A1.o5, A1.06, A1.07, A1.09, A1.10, A1.13, A1.14, A1.15, A1.16, A1.21, A1.23. A1.24, A1.25, A1.75, A1.76, A1.78, A1.80, A.107, A1.108, A2.03, A2.04, A2.09, A2.10, A2.16, A3.02 and A3.03 completely inhibit fungal infestation in this test.

D-2: Action against Phylophthora on Tomato Plants a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and 20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and 20° C. Compounds of Tables 1 to 37 exhibit a long-lasting effect against fungus infestation. Compounds A1.02, A1.03, A1.04, A1.03, A1.o5, A1.06, A1.07, A1.09, A1.10, A1.13, A1.14, A1.15, A1.16, A1.21, A1.23. A1.24, A1.25, A1.75, A1.76, A1.78, A1.80, A.107, A1.108, A2.03, A2.04, A2.09, A2.10, A2.16, A3.02 and A3.03 completely inhibit fungal infestation in this test.

D-3: Action against Phytophthora on Potato Plants a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and 20° C. Fungal infestation is effectively controlled with compounds of Tables 1 to 37.

Compounds A1.02, A1.03, A1.04, A1.03, A1.o5, A1.06, A1.07, A1.09, A1.10, A1.13, A1.14, A1.15, A1.16, A1.21, A1.23. A1.24, A1.25, A1.75, A1.76, A1.78, A1.80, A.107, A1.108, A2.03, A2.04, A2.09, A2.10, A2.16, A3.02 and A3.03 completely inhibit fungal infestation in this test.

What is claimed is:

1. α-Sulfin- and α-sulfonamino acid amides of formula I (I)

$$R_1-\underset{O}{\overset{(O)_n}{\underset{\|}{S}}}-\underset{H}{N}-\underset{R_3}{\overset{R_2}{C}}-\overset{O}{\overset{\|}{C}}-\underset{H}{N}-\underset{R_5}{\overset{R_4}{\underset{|}{C}}}\underset{R_7}{\overset{R_6}{\underset{|}{C}}}-\underset{\underset{O-R_8}{|}}{\overset{R_9}{\underset{R_{10}}{\text{Ar}}}}-O-R_{11}$$

including the optical isomers thereof and mixtures of such isomers, wherein n is a number zero or one;

R$_1$ is C$_1$–C$_{12}$alkyl, C$_1$–C$_{12}$alkyl substituted with C$_1$–C$_4$alkoxy, C$_1$–C$_4$alkylthio, C$_1$–C$_4$alkylsulfonyl, C$_3$–C$_8$cycloalkyl, cyano, C$_1$–C$_6$alkoxycarbonyl, C$_3$–C$_6$alkenyloxycarbonyl or C$_3$–C$_6$alkynyloxycarbonyl; C$_3$–C$_8$cycloalkyl; C$_2$–C$_{12}$alkenyl; C$_2$–C$_{12}$alkynyl; C$_1$–C$_{12}$haloalkyl; or a group NR$_{12}$R$_{13}$ wherein R$_{12}$ and R$_{13}$ are each independently of the other hydrogen or C$_1$–C$_6$-alkyl, or together are tetra- or penta-methylene;

$R_2$ and $R_3$ are each independently hydrogen; $C_1-C_8$alkyl; $C_1-C_8$alkyl substituted with hydroxy, mercapto, $C_1-C_4$alkoxy or $C_1-C_4$alkylthio; $C_3-C_8$alkenyl; $C_3-C_8$alkynyl; $C_3C_8$cycloalkyl; $C_3-C_8$cycloalkyl-$C_1-C_4$alkyl; or the two groups $R_2$ and $R_3$ together with the carbon atom to which they are bonded form a three- to eight-membered hydrocarbon ring;

$R_4$, $R_5$, $R_6$ and $R_7$ are each independently hydrogen or $C_1-C_4$alkyl;

$R_8$ is $C_1-C_6$alkyl, $C_3-C_6$alkenyl or $C_3-C_6$alkynyl;

$R_9$ and $R_{10}$ are each independently hydrogen or $C_1-C_4$alkyl; and $R_{11}$ is either

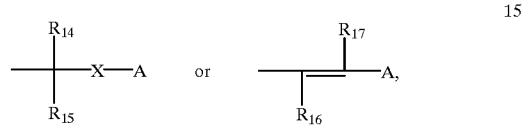

in wherein $R_{14}$, $R_{15}$, $R_{16}$ and $R_{17}$ are each independently hydrogen or $C_1-C_4$alkyl, X is oxygen, sulfur or —$NR_{18}$—, wherein $R_{18}$ is hydrogen or $C_1-C_4$alkyl, and A is optionally substituted mono- or polycylic aryl or heteroaryl.

2. A compound according to claim 1 wherein $R_1$ is $C_1-C_{12}$alkyl, $C_1-C_{12}$alkyl substituted with $C_1-C_4$alkoxy, $C_1-C_4$alkylthio, or $C_1-C_4$alkylsulfonyl; $C_2-C_{12}$alkenyl; $C_2-C_{12}$alkynyl; $C_1-C_{12}$haloalkyl; or a group $NR_{12}R_{13}$ wherein $R_{12}$ and $R_{13}$ are each independently of the other hydrogen or $C_1-C_6$-alkyl, or together are tetra- or penta-methylene; and $R_2$ is hydrogen and $R_3$ is $C_1-C_8$alkyl; $C_1-C_8$alkyl substituted with hydroxy, mercapto, $C_1-C_4$alkoxy or $C_1-C_4$alkylthio; $C_3-C_8$alkenyl; $C_3-C_8$alkynyl; $C_3-C_8$cycloalkyl; $C_3-C_8$cycloalkyl-$C_1-C_4$alkyl; and $R_4$ is hydrogen or $C_1-C_4$alkyl and $R_5$, $R_6$ and $R_7$ are each hydrogen.

3. A compound of formula I according to claim 1 wherein n is one; and $R_1$ is $C_1-C_{12}$alkyl, $C_2-C_{12}$alkenyl; $C_1-C_{12}$haloalkyl; or a group $NR_{12}R_{13}$ wherein $R_{12}$ and $R_{13}$ are each independently of the other hydrogen or $C_1-C_6$-alkyl; and $R_2$ is hydrogen and $R_3$ is $C_1-C_4$alkyl; $C_3-C_4$alkenyl or cyclopropyl; and $R_4$ is hydrogen, methyl or ethyl and $R_5$, $R_6$ and $R_7$ are each hydrogen; and $R_8$ is $C_1-C_6$alkyl.

4. A compound of formula I according to claim 1 wherein n is one; and $R_1$ is $C_1-C_4$alkyl, $C_2-C_4$alkenyl; $C_1-C_4$haloalkyl; or $C_1-C_2$-dialkylamino; and $R_2$ is hydrogen and $R_3$ is $C_3-C_4$alkyl; allyl or cyclopropyl; and $R_4$ is hydrogen or methyl and $R_5$, $R_6$ and $R_7$ are each hydrogen; and $R_8$ is methyl or ethyl.

5. A compound of formula I according to claim 1 wherein n is one; and $R_1$ is $C_1-C_4$alkyl, vinyl; $C_1-C_4$haloalkyl; or dimethylamino; and $R_2$ is hydrogen and $R_3$ is isopropyl; and $R_4$, $R_5$, $R_6$ and $R_7$ are each hydrogen; and $R_8$ is methyl.

6. A compound of formula I according to claim 1 wherein

A is optionally substituted heteroaryl consisting of one or two five to six membered rings containing one to four identical or different heteroatoms selected from oxygen, nitrogen and sulfur.

7. A compound of formula I according to claim 1, wherein $R_9$, $R_{10}$, $R_{14}$, $R_{15}$, $R_{16}$, $R_{17}$ are each independently hydrogen or methyl; and X is oxygen, sulfur or —$NR_{18}$—, wherein $R_{18}$ is hydrogen or methyl; and A is phenyl, naphthyl, furyl, thienyl, pyrrolyl, imidazolyl, pyrazolyl, thiazolyl, oxazolyl, isoxazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl, each optionally substituted by 1 to 3 substituents selected from $C_1-C_8$-alkyl, $C_2-C_8$-alkenyl, $C_2-C_8$-alkynyl, $C_3-C_8$-cycloalkyl, $C_3-C_8$-cycloalkyl-$C_1-C_4$-alkyl, phenyl, phenyl-$C_1-C_4$-alkyl wherein the hydrogens of all the preceding substituents may be in turn optionally substituted by one or several same or different halogens; $C_1-C_8$-alkoxy; $C_3-C_8$-alkenyloxy; $C_3-C_8$-alkynyloxy; $C_1-C_8$-alkoxy-$C_1-C_4$-alkyl; $C_1-C_8$halogenalkoxy; $C_1-C_8$-alkylthio; $C_1-C_8$-halogenalkylthio; $C_1-C_8$-alkylsulfonyl; formyl; $C_2-C_8$-alkanoyl; hydroxy; halogen; cyano; nitro; amino; $C_1-C_8$-alkylamino; $C_1-C_8$-dialkylamino; carboxy; $C_1-C_8$-alkoxycarbonyl; $C_1-C_8$-alkenyloxycarbonyl or $C_1-C_8$-alkynyloxycarbonyl.

8. A compound of formula I according to claim 1, wherein $R_9$, $R_{10}$, $R_{14}$, $R_{15}$, $R_{16}$, $R_{17}$ are each hydrogen; and X is oxygen, sulfur or —NH—; or A is phenyl, naphthyl, thienyl, pyridyl, pyrimidinyl, triazinyl or quinolyl, each optionally substituted by 1 to 3 substituents selected from $C_1-C_8$-alkyl, $C_2-C_8$-alkenyl wherein the hydrogens of all the preceding substituents may be in turn optionally substituted by one or several same or different halogens; $C_1-C_8$-alkoxy; $C_1-C_8$halogenalkoxy; $C_1-C_8$-alkylthio; $C_1-C_8$-halogenalkylthio; halogen; cyano; nitro or $C_1-C_8$-alkoxycarbonyl.

9. A compound of formula I according to claim 1, wherein $R_9$, $R_{10}$, $R_{14}$, $R_{15}$, $R_{16}$, $R_{17}$ are each hydrogen; and X is oxygen; and A is phenyl or pyridyl, each optionally substituted by 1 to 3 substituents selected from $C_1-C_8$-alkyl; $C_1-C_8$-haloalkyl; $C_1-C_8$-alkoxy; $C_1-C_8$halogenalkoxy; $C_1-C_8$-alkylthio; $C_1-C_8$-halogenalkylthio; halogen; cyano; nitro or $C_1-C_8$-alkoxycarbonyl.

10. A process for the preparation of a compound of formula I according to claim 1, which comprises reacting a) an amino acid of formula II or a carboxy-activated derivative thereof

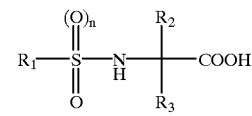

(II)

wherein $R_1$, n, $R_2$ and $R_3$ are as defined for formula I is reacted with an amine of formula III

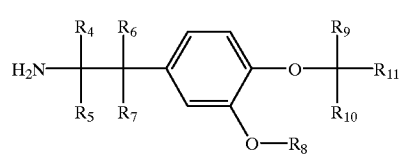
(III)

wherein $R_4$, $R_5$, $R_6$, $R_7$, $R_8$, $R_9$, $R_{10}$ and $R_{11}$ are as defined for formula I optionally in the presence of a base and optionally in the presence of a diluting agent, or b) an amino acid derivative of formula VI

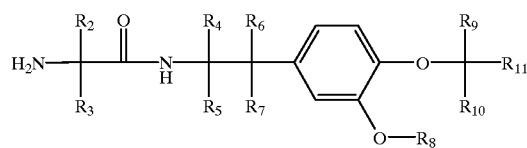
(VI)

wherein $R_2$, $R_3$, $R_4$, $R_5$, $R_6$, $R_7$, $R_8$, $R_9$, $R_{10}$ and $R_{11}$ are as defined for formula I with a sulfonyl halide or a sulfinyl halide of formula V

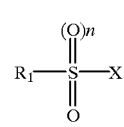
(V)

wherein $R_1$ and n are as defined for formula I and X is halide, preferentially chlorine or bromine, or c) a phenol of formula VII

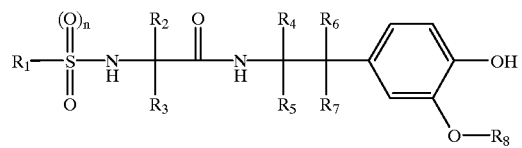
(VII)

wherein $R_1$, n, $R_2$, $R_3$, $R_4$, $R_5$, $R_6$, $R_7$ and $R_8$ are as defined for formula I with a compound of formula VIII

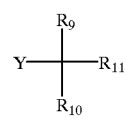
(VIII)

wherein $R_9$, $R_{10}$ and $R_{11}$ are as defined for formula I and Y is a leaving group like a halide such as a chloride or bromide or a sulfonic ester such as a tosylate, mesylate or triflate.

11. A process for the preparation of a compound of formula Ia

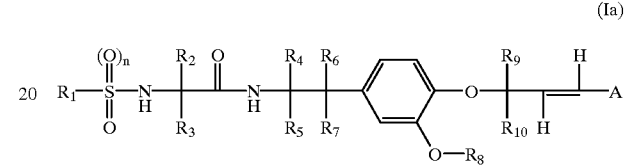
(Ia)

wherein $R_1$, n, $R_2$, $R_3$, $R_4$, $R_5$, $R_6$, $R_7$, $R_8$, $R_9$, $R_{10}$ and A are defined in claim 1 for formula I which comprises reacting a compound of formula IX (IX)

wherein $R_1$, n, $R_2$, $R_3$, $R_4$, $R_5$, $R_6$, $R_7$, $R_8$, $R_9$, $R_{10}$ and A are defined for formula I with hydrogen.

12. A composition for controlling and protecting against phytopathogenic microorganisms, comprising a compound of formula I according to claim 1 as active ingredient together with a suitable carrier.

13. A method of controlling and preventing an infestation of crop plants by phytopathogenic microorganisms, preferably fungal organisms, which comprises the application of a compound of formula I according to claim 1 as active ingredient to the plant, to parts of plants or to the locus thereof.

* * * * *